US008623349B2

(12) United States Patent
Fernandez Herrero et al.

(10) Patent No.: US 8,623,349 B2
(45) Date of Patent: Jan. 7, 2014

(54) SYSTEMS, METHODS AND MICRORGANISMS FOR ANTIBODY PRODUCTION WITH TYPE III SECRETION SYSTEM

(75) Inventors: Luis Angel Fernandez Herrero, Madrid (ES); Ana Blanco Toribio, Madrid (ES)

(73) Assignee: Consejo Superior de Investigaciones Cientificas, Madrid (ES)

( * ) Notice: Subject to any disclaimer, the term of this patent is extended or adjusted under 35 U.S.C. 154(b) by 998 days.

(21) Appl. No.: 12/531,022

(22) PCT Filed: Mar. 12, 2008

(86) PCT No.: PCT/ES2008/070045

§ 371 (c)(1), (2), (4) Date: Dec. 17, 2009

(87) PCT Pub. No.: WO2008/110653

PCT Pub. Date: Sep. 18, 2008

(65) Prior Publication Data

US 2010/0120124 A1 May 13, 2010

(30) Foreign Application Priority Data

Mar. 12, 2007 (ES) .................................. 200700644

(51) Int. Cl.

| | |
|---|---|
| ***A01N 63/00*** | (2006.01) |
| ***A61K 48/00*** | (2006.01) |
| ***A61K 39/02*** | (2006.01) |
| ***A01N 65/00*** | (2009.01) |
| ***A61K 45/00*** | (2006.01) |
| ***A61K 47/00*** | (2006.01) |
| ***A61K 51/00*** | (2006.01) |
| ***A61M 36/14*** | (2006.01) |
| ***A61K 39/395*** | (2006.01) |
| ***A61K 39/00*** | (2006.01) |
| ***A61K 39/38*** | (2006.01) |

(52) U.S. Cl.

USPC ...... 424/93.2; 424/93.4; 424/200.1; 424/809; 424/93.1; 424/278.1; 424/1.49; 424/130.1; 424/178.1; 424/184.1

(58) Field of Classification Search

None

See application file for complete search history.

(56) References Cited

PUBLICATIONS

Spears et al., FEMS Microbiol Lett, 2006; 255: 187-202.*
Fernández, L.A. Prokaryotic expression of antibodies and affibodies. Curr Opin Biotechnol 15, 364-373 (2004).
Laffly, E. & Sodoyer, R. Monoclonal and recombinant antibodies, 30 years after. Hum Antibodies 14, 33-55 (2005).
Wu, A.M. & Senter, P.D. Arming antibodies: prospects and challenges for immunoconjugates. Nat Biotechnol 23, 1137-1146 (2005).
Holliger, P. & Hudson, P.J. Engineered antibody fragments and the rise of single domains. Nat Biotechnol 23, 1126-1136 (2005).
Hoogenboom, H.R. Selecting and screening recombinant antibody libraries. Nat Biotechnol 23, 1105-1116 (2005).
Muyldermans, S., Cambillau, C. & Wyns, L. Recognition of antigens by single-domain antibody fragments: the superfluous luxury of paired domains. Trends Biochem Sci 26, 230-235. (2001).
Reff, M.E. & Heard, C. A review of modifications to recombinant antibodies: attempt to increase efficacy in oncology applications. Crit Rev Oncol Hematol 40, 25-35. (2001).
Noel, D. et al. High in vivo production of a model monoclonal antibody on adenoviral gene transfer. Hum Gene Ther 13, 1483-1493 (2002).
Lobato, M.N. & Rabbitts, T.H. Intracellular antibodies and challenges facing their use as therapeutic agents. Trends Mol Med 9, 390-396 (2003).
Pawelek, J.M., Low, K.B. & Bermudes, D. Bacteria as tumour-targeting vectors. Lancet Oncol 4, 548-556 (2003).
Dooley, H., Flajnik, M.F. & Porter, A.J. Selection and characterization of naturally occurring single-domain (IgNAR) antibody fragments from immunized sharks by phage display. Mol Immunol 40, 25-33. (2003).
Muyldermans, S. Single domain camel antibodies: current status. J Biotechnol 74, 277-302. (2001).
Kaper, J.B., Nataro, J.P. & Mobley, H.L. Pathogenic *Escherichia coli*. Nature Reviews Microbiology 2, 123-139 (2004).
Spears, K.J., Roe, A.J. & Gaily, D.L. A comparison of enteropathogenic and enterohaemorrhagic *Escherichia coli* pathogenesis. FEMS Microbiol Lett 255, 187-202 (2006).
Cornelis, G.R. The type III secretion injectisome. Nat Rev Microbiol 4, 811-825 (2006).
Galan, J.E. & Wolf-Watz, H. Protein delivery into eukaryotic cells by type III secretion machines. Nature 444, 567-573 (2006).
Garmendia, J., Frankel, G. & Crepin, V.F. Enteropathogenic and enterohemorrhagic *Escherichia coli* infections: translocation, translocation, translocation. Infect Immun 73, 2573-2585 (2005).
Chen, H.D. & Frankel, G. Enteropathogenic *Escherichia coli*: unravelling pathogenesis. FEMS Microbiol Rev 29, 83-98 (2005).
Chen, L.M., Briones, G., Donis, R.O. & Galan, J.E. Optimization of the delivery of heterologous proteins by the *Salmonella enterica* serovar Typhimurium type III secretion system for vaccine development. Infect Immun 74, 5826-5833 (2006).
Konjufca, V., Wanda, S.Y., Jenkins, M.C. & Curtiss, R., 3rd A recombinant attenuated *Salmonella enterica* serovar Typhimurium vaccine encoding *Eimeria acervulina* antigen offers protection against *E. acervulina* challenge. Infect Immun 74, 6785-6796 (2006).
Rüssmann, H. & Panthel, K. "One size fits it all": translocation of foreign antigens by Yersinia type III secretion system (TTSS) leads to concomitant CD4 and CD8 T-cell priming. Int J Med Microbiol 294, 313-317 (2004).
Rüssmann, H. et al. Attenuated *Yersinia pseudotuberculosis* carrier vaccine for simultaneous antigen-specific CD4 and CD8 T-cell induction. Infect Immun 71, 3463-3472 (2003).

(Continued)

*Primary Examiner* — Vanessa L. Ford
*Assistant Examiner* — Lakia Tongue
(74) *Attorney, Agent, or Firm* — K&L Gates LLP

(57) ABSTRACT

Exemplary embodiments disclosed herein include a microorganism that produces, secretes and injects recombinant antibodies into eukaryote cells said the described microorganisms can be used to prepare pharmaceutical compositions for the treatment of human or veterinary diseases.

6 Claims, 8 Drawing Sheets

(56) References Cited

PUBLICATIONS

Rüssmann, H. *Yersinia* outer protein E, YopE.A versatile type III effector molecule for cytosolic targeting of heterologous antigens by attenuated *Salmonella*. Adv Exp Med Biol 529, 407-413 (2003).

Evans, D.T. et al. Mucosal priming of simian immunodeficiency virus-specific cytotoxic T-lymphocyte responses in *Rhesus macaques* by the *Salmonella* type III secretion antigen delivery system. J Virol 77, 2400-2409 (2003).

Rüssmann, H. et al. Protection against murine listeriosis by oral vaccination with recombinant *Salmonella* expressing hybrid *Yersinia* type III proteins. J Immunol 167, 357-365 (2001).

Rüssmann, H. et al. Delivery of epitopes by the *Salmonella* type III secretion system for vaccine development. Science 281, 565-568 (1998).

Kotton, C.N. et al. Safety and immunogenicity of attenuated *Salmonella enterica* serovar *Typhimurium* delivering an HIV-1 Gag antigen via the *Salmonella* Type III secretion system. Vaccine 24, 6216-6224 (2006).

Nishikawa, H. et al. In vivo antigen delivery by a *Salmonella typhimurium* type III secretion system for therapeutic cancer vaccines. J Clin Invest 116, 1946-1954 (2006).

Charpentier, X. & Oswald, E. Identification of the secretion and translocation domain of the enteropathogenic and enterohemorrhagic *Escherichia coli* effector Cif, using TEM-1 beta-lactamase as a new fluorescence-based reporter. J Bacteriol 186, 5486-5495 (2004).

Garmendia, J. et al. TccP is an enterohaemorrhagic *Escherichia coli* O157:H7 type III effector protein that couples Tir to the actin-cytoskeleton. Cell Microbiol 6, 1167-1183 (2004).

Ausubel, F.M. et al. Short Protocols in Molecular Biology, Edn. Third Edition. (John Wiley & Sons, Inc., New York; 1997), Unit 10.6; p. 10-45 to 10-50.

Schlosser-Silverman, E., Elgrably-Weiss, M., Rosenshine, I., Kohen, R. & Altuvia, S. Characterization of *Escherichia coli* DNA lesions generated within J774 macrophages. J Bacteriol 182, 5225-5230 (2000).

Jurado, P., Ritz, D., Beckwith, J., de Lorenzo, V. & Fernández, L.A. Production of functional single-chain Fv antibodies in the cytoplasm of *Escherichia coli*. J Mol Biol 320, 1-10. (2002).

Wilson, R.K., Shaw, R.K., Daniell, S., Knutton, S. & Frankel, G. Role of EscF, a putative needle complex protein, in the type III protein translocation system of enteropathogenic *Escherichia coli*. Cell Microbiol 3, 753-762 (2001).

* cited by examiner

SEQUENCE LISTING

```
<160> NUMBER OF SEQ ID NOS: 12

<210> SEQ ID NO 1
<211> LENGTH: 585
<212> TYPE: DNA
<213> ORGANISM: Artificial
<220> FEATURE:
<223> OTHER INFORMATION: EspF-Vamy fusion
<220> FEATURE:
<221> NAME/KEY: CDS
<222> LOCATION: (27)..(575)
<223> OTHER INFORMATION: EspF-Vamy fusion
<220> FEATURE:
<221> NAME/KEY: misc_feature
<222> LOCATION: (27)..(86)
<223> OTHER INFORMATION: Type III secretion signal sequence
<220> FEATURE:
<221> NAME/KEY: misc_feature
<222> LOCATION: (87)..(500)
<223> OTHER INFORMATION: VHH anti-amilase (Vamy) antibody sequence
<220> FEATURE:
<221> NAME/KEY: misc_feature
<222> LOCATION: (501)..(518)
<223> OTHER INFORMATION: 6xHis-tag sequence
<220> FEATURE:
<221> NAME/KEY: misc_feature
<222> LOCATION: (519)..(575)
<223> OTHER INFORMATION: Sequence E-tag

<400> SEQUENCE: 1

gaattctcta gaaagaggca taaatt atg ctt aat gga att agt aac gct gct      53
                             Met Leu Asn Gly Ile Ser Asn Ala Ala
                             1               5

tct aca cta ggg cgg cag ctt gta ggt atc gca gcg gcc cag ccg gcc      101
Ser Thr Leu Gly Arg Gln Leu Val Gly Ile Ala Ala Ala Gln Pro Ala
10                  15                  20                  25

atg gct cag gtg cag ctg gtg gag tct tgg gga ggc tcg gtg cag gct      149
Met Ala Gln Val Gln Leu Val Glu Ser Trp Gly Gly Ser Val Gln Ala
                30                  35                  40

ggg ggg tct ctg aga ctc tcc tgc aca gcc cct gga ttc acc tcc aat      197
Gly Gly Ser Leu Arg Leu Ser Cys Thr Ala Pro Gly Phe Thr Ser Asn
            45                  50                  55

agc tgc cgc atg gac tgg tac cgc cag gct gca ggg aag cag cgc gag      245
Ser Cys Arg Met Asp Trp Tyr Arg Gln Ala Ala Gly Lys Gln Arg Glu
        60                  65                  70

tgg gtc tca tct att agt act gat ggt cgc aca agc tat gca gac tcc      293
Trp Val Ser Ser Ile Ser Thr Asp Gly Arg Thr Ser Tyr Ala Asp Ser
    75                  80                  85

gtg aag ggc cga ttc acc atc tcc aaa gac aaa gcc aag gac acg gtg      341
Val Lys Gly Arg Phe Thr Ile Ser Lys Asp Lys Ala Lys Asp Thr Val
```

-continued

```
90                  95                  100                 105

tat ctg caa atg aac agc ctg aaa cct gag gac acg gcc atc tat tac        389
Tyr Leu Gln Met Asn Ser Leu Lys Pro Glu Asp Thr Ala Ile Tyr Tyr
                110                 115                 120

tgt gcc gtg agg acg aat ggg tat cgt ccg caa tct cac gaa ttt cgc        437
Cys Ala Val Arg Thr Asn Gly Tyr Arg Pro Gln Ser His Glu Phe Arg
            125                 130                 135

tac tgg ggc ccg ggg acc cag gtc acc gtc tcc tca gcg gcc gca tcg        485
Tyr Trp Gly Pro Gly Thr Gln Val Thr Val Ser Ser Ala Ala Ala Ser
        140                 145                 150

ggg gcc gcg tcg acg cac cat cac cat cac cat gct tcg acg ccc ggg        533
Gly Ala Ala Ser Thr His His His His His His Ala Ser Thr Pro Gly
    155                 160                 165

ggt gcg ccg gtg ccg tat ccg gat ccg ctg gaa ccg gcc taa                575
Gly Ala Pro Val Pro Tyr Pro Asp Pro Leu Glu Pro Ala
170                 175                 180

tgagaattcc                                                             585


<210> SEQ ID NO 2
<211> LENGTH: 182
<212> TYPE: PRT
<213> ORGANISM: Artificial
<220> FEATURE:
<223> OTHER INFORMATION: Synthetic construct

<400> SEQUENCE: 2

Met Leu Asn Gly Ile Ser Asn Ala Ala Ser Thr Leu Gly Arg Gln Leu
1               5                   10                  15

Val Gly Ile Ala Ala Ala Gln Pro Ala Met Ala Gln Val Gln Leu Val
            20                  25                  30

Glu Ser Trp Gly Gly Ser Val Gln Ala Gly Gly Ser Leu Arg Leu Ser
        35                  40                  45

Cys Thr Ala Pro Gly Phe Thr Ser Asn Ser Cys Arg Met Asp Trp Tyr
    50                  55                  60

Arg Gln Ala Ala Gly Lys Gln Arg Glu Trp Val Ser Ser Ile Ser Thr
65                  70                  75                  80

Asp Gly Arg Thr Ser Tyr Ala Asp Ser Val Lys Gly Arg Phe Thr Ile
                85                  90                  95

Ser Lys Asp Lys Ala Lys Asp Thr Val Tyr Leu Gln Met Asn Ser Leu
            100                 105                 110

Lys Pro Glu Asp Thr Ala Ile Tyr Tyr Cys Ala Val Arg Thr Asn Gly
        115                 120                 125

Tyr Arg Pro Gln Ser His Glu Phe Arg Tyr Trp Gly Pro Gly Thr Gln
    130                 135                 140

Val Thr Val Ser Ser Ala Ala Ala Ser Gly Ala Ala Ser Thr His His
145                 150                 155                 160

His His His His Ala Ser Thr Pro Gly Gly Ala Pro Val Pro Tyr Pro
                165                 170                 175

Asp Pro Leu Glu Pro Ala
            180


<210> SEQ ID NO 3
<211> LENGTH: 564
<212> TYPE: DNA
<213> ORGANISM: Artificial
<220> FEATURE:
<223> OTHER INFORMATION: EspF-Vgfg fusion
<220> FEATURE:
<221> NAME/KEY: CDS
<222> LOCATION: (27)..(554)
```

```
<220> FEATURE:
<221> NAME/KEY: misc_feature
<222> LOCATION: (27)..(86)
<223> OTHER INFORMATION: Type III secretion signal sequence
<220> FEATURE:
<221> NAME/KEY: misc_feature
<222> LOCATION: (87)..(479)
<223> OTHER INFORMATION: VHH anti-GFP antibody sequence
<220> FEATURE:
<221> NAME/KEY: misc_feature
<222> LOCATION: (480)..(497)
<223> OTHER INFORMATION: 6xHis-tag sequence
<220> FEATURE:
<221> NAME/KEY: misc_feature
<222> LOCATION: (498)..(554)
<223> OTHER INFORMATION: Sequence E-tag

<400> SEQUENCE: 3

gaattctcta gaaagaggca taaatt atg ctt aat gga att agt aac gct gct      53
                             Met Leu Asn Gly Ile Ser Asn Ala Ala
                             1               5

tct aca cta ggg cgg cag ctt gta ggt atc gca gcg gcc cag ccg gcc      101
Ser Thr Leu Gly Arg Gln Leu Val Gly Ile Ala Ala Ala Gln Pro Ala
10                  15                  20                  25

atg gct cag gtg cag ctg gtg gag tct ggg gga gcc ttg gtg cag ccg      149
Met Ala Gln Val Gln Leu Val Glu Ser Gly Gly Ala Leu Val Gln Pro
                30                  35                  40

ggg ggg tct ctg aga ctc tcc tgt gca gcc tct gga ttc ccc gtc aat      197
Gly Gly Ser Leu Arg Leu Ser Cys Ala Ala Ser Gly Phe Pro Val Asn
            45                  50                  55

cgc tat agt atg agg tgg tac cgc cag gct cca ggg aag gag cgc gag      245
Arg Tyr Ser Met Arg Trp Tyr Arg Gln Ala Pro Gly Lys Glu Arg Glu
        60                  65                  70

tgg gtc gcg ggt atg agt agt gct ggt gat cgt tca agt tat gaa gac      293
Trp Val Ala Gly Met Ser Ser Ala Gly Asp Arg Ser Ser Tyr Glu Asp
    75                  80                  85

tcc gtg aag ggc cga ttc acc atc tcc aga gac gac gcc agg aat acg      341
Ser Val Lys Gly Arg Phe Thr Ile Ser Arg Asp Asp Ala Arg Asn Thr
90                  95                  100                 105

gtg tat ctg caa atg aac agc ctg aaa cct gag gac acg gcc gtg tat      389
Val Tyr Leu Gln Met Asn Ser Leu Lys Pro Glu Asp Thr Ala Val Tyr
                110                 115                 120

tac tgt aat gtc aat gtg ggc ttt gag tac tgg ggc cag ggg acc cag      437
Tyr Cys Asn Val Asn Val Gly Phe Glu Tyr Trp Gly Gln Gly Thr Gln
            125                 130                 135

gtc acc gtc tcc tca gcg gcc gca tcg ggg gcc gcg tcg acg cac cat      485
Val Thr Val Ser Ser Ala Ala Ala Ser Gly Ala Ala Ser Thr His His
        140                 145                 150

cac cat cac cat gct tcg acg ccc ggg ggt gcg ccg gtg ccg tat ccg      533
His His His His Ala Ser Thr Pro Gly Gly Ala Pro Val Pro Tyr Pro
    155                 160                 165

gat ccg ctg gaa ccg gcc taa tgagaattcc                               564
Asp Pro Leu Glu Pro Ala
170                 175


<210> SEQ ID NO 4
<211> LENGTH: 175
<212> TYPE: PRT
<213> ORGANISM: Artificial
<220> FEATURE:
<223> OTHER INFORMATION: Synthetic construct

<400> SEQUENCE: 4

Met Leu Asn Gly Ile Ser Asn Ala Ala Ser Thr Leu Gly Arg Gln Leu
1               5                   10                  15
```

-continued

```
Val Gly Ile Ala Ala Ala Gln Pro Ala Met Ala Gln Val Gln Leu Val
            20                  25                  30

Glu Ser Gly Gly Ala Leu Val Gln Pro Gly Gly Ser Leu Arg Leu Ser
        35                  40                  45

Cys Ala Ala Ser Gly Phe Pro Val Asn Arg Tyr Ser Met Arg Trp Tyr
    50                  55                  60

Arg Gln Ala Pro Gly Lys Glu Arg Glu Trp Val Ala Gly Met Ser Ser
65                  70                  75                  80

Ala Gly Asp Arg Ser Ser Tyr Glu Asp Ser Val Lys Gly Arg Phe Thr
                85                  90                  95

Ile Ser Arg Asp Asp Ala Arg Asn Thr Val Tyr Leu Gln Met Asn Ser
            100                 105                 110

Leu Lys Pro Glu Asp Thr Ala Val Tyr Tyr Cys Asn Val Asn Val Gly
        115                 120                 125

Phe Glu Tyr Trp Gly Gln Gly Thr Gln Val Thr Val Ser Ser Ala Ala
    130                 135                 140

Ala Ser Gly Ala Ala Ser Thr His His His His His His Ala Ser Thr
145                 150                 155                 160

Pro Gly Gly Ala Pro Val Pro Tyr Pro Asp Pro Leu Glu Pro Ala
                165                 170                 175


<210> SEQ ID NO 5
<211> LENGTH: 60
<212> TYPE: DNA
<213> ORGANISM: Artificial
<220> FEATURE:
<223> OTHER INFORMATION: EspF20 sequence
<220> FEATURE:
<221> NAME/KEY: CDS
<222> LOCATION: (1)..(60)

<400> SEQUENCE: 5

atg ctt aat gga att agt aac gct gct tct aca cta ggg cgg cag ctt      48
Met Leu Asn Gly Ile Ser Asn Ala Ala Ser Thr Leu Gly Arg Gln Leu
1               5                   10                  15

gta ggt atc gca                                                      60
Val Gly Ile Ala
            20


<210> SEQ ID NO 6
<211> LENGTH: 20
<212> TYPE: PRT
<213> ORGANISM: Artificial
<220> FEATURE:
<223> OTHER INFORMATION: Synthetic construct

<400> SEQUENCE: 6

Met Leu Asn Gly Ile Ser Asn Ala Ala Ser Thr Leu Gly Arg Gln Leu
1               5                   10                  15

Val Gly Ile Ala
            20


<210> SEQ ID NO 7
<211> LENGTH: 489
<212> TYPE: DNA
<213> ORGANISM: Artificial
<220> FEATURE:
<223> OTHER INFORMATION: MutVgfp
<220> FEATURE:
<221> NAME/KEY: CDS
<222> LOCATION: (27)..(479)

<400> SEQUENCE: 7
```

-continued

```
gaattctcta gaaagaggca taaatt atg gct cag gtg cag ctg gtg gag tct       53
                             Met Ala Gln Val Gln Leu Val Glu Ser
                             1               5

ggg gga gcc ttg gtg cag ccg ggg ggg tct ctg aga ctc tcc tgt gca       101
Gly Gly Ala Leu Val Gln Pro Gly Gly Ser Leu Arg Leu Ser Cys Ala
10                  15                  20                  25

gcc tct gga ttc ccc gtc aat cgc tat agt atg agg tgg tac cgc cag       149
Ala Ser Gly Phe Pro Val Asn Arg Tyr Ser Met Arg Trp Tyr Arg Gln
                30                  35                  40

gct cca ggg aag gag cgc gag tgg gtc gcg ggt atg agt agt gct ggt       197
Ala Pro Gly Lys Glu Arg Glu Trp Val Ala Gly Met Ser Ser Ala Gly
            45                  50                  55

gat cgt tca agt tat gaa gac tcc gtg aag ggc cga ttc acc atc tcc       245
Asp Arg Ser Ser Tyr Glu Asp Ser Val Lys Gly Arg Phe Thr Ile Ser
        60                  65                  70

aga gac gac gcc agg aat acg gtg tat ctg caa atg aac agc ctg aaa       293
Arg Asp Asp Ala Arg Asn Thr Val Tyr Leu Gln Met Asn Ser Leu Lys
    75                  80                  85

cct gag gac acg gcc gtg tat tac tgt aat gtc aat gtg ggc ttt gag       341
Pro Glu Asp Thr Ala Val Tyr Tyr Cys Asn Val Asn Val Gly Phe Glu
90                  95                  100                 105

tac tgg ggc cag ggg acc cag gtc acc gtc tcc tca gcg gcc gca tcg       389
Tyr Trp Gly Gln Gly Thr Gln Val Thr Val Ser Ser Ala Ala Ala Ser
                110                 115                 120

ggg gcc gcg tcg acg cac cat cac cat cac cat gct tcg acg ccc ggg       437
Gly Ala Ala Ser Thr His His His His His His Ala Ser Thr Pro Gly
            125                 130                 135

ggt gcg ccg gtg ccg tat ccg gat ccg ctg gaa ccg gcc taa               479
Gly Ala Pro Val Pro Tyr Pro Asp Pro Leu Glu Pro Ala
        140                 145                 150

tgagaattcc                                                            489


<210> SEQ ID NO 8
<211> LENGTH: 150
<212> TYPE: PRT
<213> ORGANISM: Artificial
<220> FEATURE:
<223> OTHER INFORMATION: Synthetic construct

<400> SEQUENCE: 8

Met Ala Gln Val Gln Leu Val Glu Ser Gly Gly Ala Leu Val Gln Pro
1               5                   10                  15

Gly Gly Ser Leu Arg Leu Ser Cys Ala Ala Ser Gly Phe Pro Val Asn
            20                  25                  30

Arg Tyr Ser Met Arg Trp Tyr Arg Gln Ala Pro Gly Lys Glu Arg Glu
        35                  40                  45

Trp Val Ala Gly Met Ser Ser Ala Gly Asp Arg Ser Ser Tyr Glu Asp
    50                  55                  60

Ser Val Lys Gly Arg Phe Thr Ile Ser Arg Asp Asp Ala Arg Asn Thr
65                  70                  75                  80

Val Tyr Leu Gln Met Asn Ser Leu Lys Pro Glu Asp Thr Ala Val Tyr
                85                  90                  95

Tyr Cys Asn Val Asn Val Gly Phe Glu Tyr Trp Gly Gln Gly Thr Gln
            100                 105                 110

Val Thr Val Ser Ser Ala Ala Ala Ser Gly Ala Ala Ser Thr His His
        115                 120                 125

His His His His Ala Ser Thr Pro Gly Gly Ala Pro Val Pro Tyr Pro
    130                 135                 140

Asp Pro Leu Glu Pro Ala
```

```
145                 150


<210> SEQ ID NO 9
<211> LENGTH: 883
<212> TYPE: DNA
<213> ORGANISM: Artificial
<220> FEATURE:
<223> OTHER INFORMATION: EspF-bla
<220> FEATURE:
<221> NAME/KEY: CDS
<222> LOCATION: (6)..(866)

<400> SEQUENCE: 9

tccat atg ctt aat gga att agt aac gct gct tct aca cta ggg cgg cag      50
      Met Leu Asn Gly Ile Ser Asn Ala Ala Ser Thr Leu Gly Arg Gln
      1               5                   10                  15

ctt gta ggt atc gca gag aat tcg cac cca gaa acg ctg gtg aaa gta       98
Leu Val Gly Ile Ala Glu Asn Ser His Pro Glu Thr Leu Val Lys Val
                20                  25                  30

aaa gat gct gaa gat cag ttg ggt gca cga gtg ggt tac atc gaa ctg      146
Lys Asp Ala Glu Asp Gln Leu Gly Ala Arg Val Gly Tyr Ile Glu Leu
            35                  40                  45

gat ctc aac agc ggt aag atc ctt gag agt ttt cgc ccc gaa gaa cgt      194
Asp Leu Asn Ser Gly Lys Ile Leu Glu Ser Phe Arg Pro Glu Glu Arg
        50                  55                  60

ttt cca atg atg agc act ttt aaa gtt ctg cta tgt ggc gcg gta tta      242
Phe Pro Met Met Ser Thr Phe Lys Val Leu Leu Cys Gly Ala Val Leu
    65                  70                  75

tcc cgt att gac gcc ggg caa gag caa ctc ggt cgc cgc ata cac tat      290
Ser Arg Ile Asp Ala Gly Gln Glu Gln Leu Gly Arg Arg Ile His Tyr
80                  85                  90                  95

tct cag aat gac ttg gtt gag tac tca cca gtc aca gaa aag cat ctt      338
Ser Gln Asn Asp Leu Val Glu Tyr Ser Pro Val Thr Glu Lys His Leu
                100                 105                 110

acg gat ggc atg aca gta aga gaa tta tgc agt gct gcc ata acc atg      386
Thr Asp Gly Met Thr Val Arg Glu Leu Cys Ser Ala Ala Ile Thr Met
            115                 120                 125

agt gat aac act gcg gcc aac tta ctt ctg aca acg atc gga gga ccg      434
Ser Asp Asn Thr Ala Ala Asn Leu Leu Leu Thr Thr Ile Gly Gly Pro
        130                 135                 140

aag gag cta acc gct ttt ttg cac aac atg ggg gat cat gta act cgc      482
Lys Glu Leu Thr Ala Phe Leu His Asn Met Gly Asp His Val Thr Arg
    145                 150                 155

ctt gat cgt tgg gaa ccg gag ctg aat gaa gcc ata cca aac gac gag      530
Leu Asp Arg Trp Glu Pro Glu Leu Asn Glu Ala Ile Pro Asn Asp Glu
160                 165                 170                 175

cgt gac acc acg atg cct gta gca atg gca aca acg ttg cgc aaa cta      578
Arg Asp Thr Thr Met Pro Val Ala Met Ala Thr Thr Leu Arg Lys Leu
                180                 185                 190

tta act ggc gaa cta ctt act cta gct tcc cgg caa caa tta ata gac      626
Leu Thr Gly Glu Leu Leu Thr Leu Ala Ser Arg Gln Gln Leu Ile Asp
            195                 200                 205

tgg atg gag gcg gat aaa gtt gca gga cca ctt ctg cgc tcg gcc ctt      674
Trp Met Glu Ala Asp Lys Val Ala Gly Pro Leu Leu Arg Ser Ala Leu
        210                 215                 220

ccg gct ggc tgg ttt att gct gat aaa tct gga gcc ggt gag cgt ggg      722
Pro Ala Gly Trp Phe Ile Ala Asp Lys Ser Gly Ala Gly Glu Arg Gly
    225                 230                 235

tct cgc ggt atc att gca gca ctg ggg cca gat ggt aag ccc tcc cgt      770
Ser Arg Gly Ile Ile Ala Ala Leu Gly Pro Asp Gly Lys Pro Ser Arg
240                 245                 250                 255

atc gta gtt atc tac acg acg ggg agt cag gca act atg gat gaa cga      818
```

-continued

```
Ile Val Val Ile Tyr Thr Thr Gly Ser Gln Ala Thr Met Asp Glu Arg
                260                 265                 270

aat aga cag atc gct gag ata ggt gcc tca ctg att aag cat tgg taa      866
Asn Arg Gln Ile Ala Glu Ile Gly Ala Ser Leu Ile Lys His Trp
            275                 280                 285

ctgtcagacc aagttta                                                   883
```

<210> SEQ ID NO 10
<211> LENGTH: 286
<212> TYPE: PRT
<213> ORGANISM: Artificial
<220> FEATURE:
<223> OTHER INFORMATION: Synthetic construct

<400> SEQUENCE: 10

```
Met Leu Asn Gly Ile Ser Asn Ala Ala Ser Thr Leu Gly Arg Gln Leu
1               5                   10                  15

Val Gly Ile Ala Glu Asn Ser His Pro Glu Thr Leu Val Lys Val Lys
            20                  25                  30

Asp Ala Glu Asp Gln Leu Gly Ala Arg Val Gly Tyr Ile Glu Leu Asp
        35                  40                  45

Leu Asn Ser Gly Lys Ile Leu Glu Ser Phe Arg Pro Glu Glu Arg Phe
    50                  55                  60

Pro Met Met Ser Thr Phe Lys Val Leu Leu Cys Gly Ala Val Leu Ser
65                  70                  75                  80

Arg Ile Asp Ala Gly Gln Glu Gln Leu Gly Arg Arg Ile His Tyr Ser
                85                  90                  95

Gln Asn Asp Leu Val Glu Tyr Ser Pro Val Thr Glu Lys His Leu Thr
            100                 105                 110

Asp Gly Met Thr Val Arg Glu Leu Cys Ser Ala Ala Ile Thr Met Ser
        115                 120                 125

Asp Asn Thr Ala Ala Asn Leu Leu Leu Thr Thr Ile Gly Gly Pro Lys
    130                 135                 140

Glu Leu Thr Ala Phe Leu His Asn Met Gly Asp His Val Thr Arg Leu
145                 150                 155                 160

Asp Arg Trp Glu Pro Glu Leu Asn Glu Ala Ile Pro Asn Asp Glu Arg
                165                 170                 175

Asp Thr Thr Met Pro Val Ala Met Ala Thr Thr Leu Arg Lys Leu Leu
            180                 185                 190

Thr Gly Glu Leu Leu Thr Leu Ala Ser Arg Gln Gln Leu Ile Asp Trp
        195                 200                 205

Met Glu Ala Asp Lys Val Ala Gly Pro Leu Leu Arg Ser Ala Leu Pro
    210                 215                 220

Ala Gly Trp Phe Ile Ala Asp Lys Ser Gly Ala Gly Glu Arg Gly Ser
225                 230                 235                 240

Arg Gly Ile Ile Ala Ala Leu Gly Pro Asp Gly Lys Pro Ser Arg Ile
                245                 250                 255

Val Val Ile Tyr Thr Thr Gly Ser Gln Ala Thr Met Asp Glu Arg Asn
            260                 265                 270

Arg Gln Ile Ala Glu Ile Gly Ala Ser Leu Ile Lys His Trp
        275                 280                 285
```

<210> SEQ ID NO 11
<211> LENGTH: 1354
<212> TYPE: DNA
<213> ORGANISM: Artificial
<220> FEATURE:
<223> OTHER INFORMATION: EspF-Vamy-bla

```
<220> FEATURE:
<221> NAME/KEY: CDS
<222> LOCATION: (8)..(1354)

<400> SEQUENCE: 11

ataacat atg ctt aat gga att agt aac gct gct tct aca cta ggg cgg       49
        Met Leu Asn Gly Ile Ser Asn Ala Ala Ser Thr Leu Gly Arg
        1               5                   10

cag ctt gta ggt atc gca gcg gcc cag ccg gcc atg gct cag gtg cag       97
Gln Leu Val Gly Ile Ala Ala Ala Gln Pro Ala Met Ala Gln Val Gln
15                  20                  25                  30

ctg gtg gag tct tgg gga ggc tcg gtg cag gct ggg ggg tct ctg aga      145
Leu Val Glu Ser Trp Gly Gly Ser Val Gln Ala Gly Gly Ser Leu Arg
                35                  40                  45

ctc tcc tgc aca gcc cct gga ttc acc tcc aat agc tgc cgc atg gac      193
Leu Ser Cys Thr Ala Pro Gly Phe Thr Ser Asn Ser Cys Arg Met Asp
            50                  55                  60

tgg tac cgc cag gct gca ggg aag cag cgc gag tgg gtc tca tct att      241
Trp Tyr Arg Gln Ala Ala Gly Lys Gln Arg Glu Trp Val Ser Ser Ile
        65                  70                  75

agt act gat ggt cgc aca agc tat gca gac tcc gtg aag ggc cga ttc      289
Ser Thr Asp Gly Arg Thr Ser Tyr Ala Asp Ser Val Lys Gly Arg Phe
    80                  85                  90

acc atc tcc aaa gac aaa gcc aag gac acg gtg tat ctg caa atg aac      337
Thr Ile Ser Lys Asp Lys Ala Lys Asp Thr Val Tyr Leu Gln Met Asn
95                  100                 105                 110

agc ctg aaa cct gag gac acg gcc atc tat tac tgt gcc gtg agg acg      385
Ser Leu Lys Pro Glu Asp Thr Ala Ile Tyr Tyr Cys Ala Val Arg Thr
                115                 120                 125

aat ggg tat cgt ccg caa tct cac gaa ttt cgc tac tgg ggc ccg ggg      433
Asn Gly Tyr Arg Pro Gln Ser His Glu Phe Arg Tyr Trp Gly Pro Gly
            130                 135                 140

acc cag gtc acc gtc tcc tca gcg gcc gca tcg ggg gcc gcg tcg acg      481
Thr Gln Val Thr Val Ser Ser Ala Ala Ala Ser Gly Ala Ala Ser Thr
        145                 150                 155

cac cat cac cat cac cat gct tcg acg ccc ggg ggt gcg ccg gtg ccg      529
His His His His His His Ala Ser Thr Pro Gly Gly Ala Pro Val Pro
    160                 165                 170

tat ccg gat ccg ctg gaa ccg gcc gcg aat tcg cac cca gaa acg ctg      577
Tyr Pro Asp Pro Leu Glu Pro Ala Ala Asn Ser His Pro Glu Thr Leu
175                 180                 185                 190

gtg aaa gta aaa gat gct gaa gat cag ttg ggt gca cga gtg ggt tac      625
Val Lys Val Lys Asp Ala Glu Asp Gln Leu Gly Ala Arg Val Gly Tyr
                195                 200                 205

atc gaa ctg gat ctc aac agc ggt aag atc ctt gag agt ttt cgc ccc      673
Ile Glu Leu Asp Leu Asn Ser Gly Lys Ile Leu Glu Ser Phe Arg Pro
            210                 215                 220

gaa gaa cgt ttt cca atg atg agc act ttt aaa gtt ctg cta tgt ggt      721
Glu Glu Arg Phe Pro Met Met Ser Thr Phe Lys Val Leu Leu Cys Gly
        225                 230                 235

gcg gta tta tcc cgt gtt gac gcc ggg caa gag caa ctc ggt cgc cgc      769
Ala Val Leu Ser Arg Val Asp Ala Gly Gln Glu Gln Leu Gly Arg Arg
    240                 245                 250

ata cac tat tct cag aat gac ttg gtt gag tac tca cca gtc aca gaa      817
Ile His Tyr Ser Gln Asn Asp Leu Val Glu Tyr Ser Pro Val Thr Glu
255                 260                 265                 270

aag cat ctt acg gat ggc atg aca gta aga gaa tta tgc agt gct gcc      865
Lys His Leu Thr Asp Gly Met Thr Val Arg Glu Leu Cys Ser Ala Ala
                275                 280                 285

ata acc atg agt gat aac act gct gcc aac tta ctt ctg aca acg atc      913
Ile Thr Met Ser Asp Asn Thr Ala Ala Asn Leu Leu Leu Thr Thr Ile
```

```
            290                 295                 300

gga gga ccg aag gag cta acc gct ttt ttg cac aac atg ggg gat cat      961
Gly Gly Pro Lys Glu Leu Thr Ala Phe Leu His Asn Met Gly Asp His
        305                 310                 315

gta act cgc ctt gat cgt tgg gaa ccg gag ctg aat gaa gcc ata cca     1009
Val Thr Arg Leu Asp Arg Trp Glu Pro Glu Leu Asn Glu Ala Ile Pro
    320                 325                 330

aac gac gag cgt gac acc acg atg cct gca gca atg gca aca acg ttg     1057
Asn Asp Glu Arg Asp Thr Thr Met Pro Ala Ala Met Ala Thr Thr Leu
335                 340                 345                 350

cgc aaa cta tta act ggc gaa cta ctt act cta gct tcc cgg caa caa     1105
Arg Lys Leu Leu Thr Gly Glu Leu Leu Thr Leu Ala Ser Arg Gln Gln
                355                 360                 365

tta ata gac tgg atg gag gcg gat aaa gtt gca gga cca ctt ctg cgc     1153
Leu Ile Asp Trp Met Glu Ala Asp Lys Val Ala Gly Pro Leu Leu Arg
            370                 375                 380

tcg gcc ctt ccg gct ggc tgg ttt att gct gat aaa tct gga gcc ggt     1201
Ser Ala Leu Pro Ala Gly Trp Phe Ile Ala Asp Lys Ser Gly Ala Gly
        385                 390                 395

gag cgt ggg tct cgc ggt atc att gca gca ctg ggg cca gat ggt aag     1249
Glu Arg Gly Ser Arg Gly Ile Ile Ala Ala Leu Gly Pro Asp Gly Lys
    400                 405                 410

ccc tcc cgt atc gta gtt atc tac acg acg ggg agt cag gca act atg     1297
Pro Ser Arg Ile Val Val Ile Tyr Thr Thr Gly Ser Gln Ala Thr Met
415                 420                 425                 430

gat gaa cga aat aga cag atc gct gag ata ggt gcc tca ctg att aag     1345
Asp Glu Arg Asn Arg Gln Ile Ala Glu Ile Gly Ala Ser Leu Ile Lys
                435                 440                 445

cat tgg taa                                                         1354
His Trp
```

<210> SEQ ID NO 12
<211> LENGTH: 448
<212> TYPE: PRT
<213> ORGANISM: Artificial
<220> FEATURE:
<223> OTHER INFORMATION: Synthetic construct

<400> SEQUENCE: 12

```
Met Leu Asn Gly Ile Ser Asn Ala Ala Ser Thr Leu Gly Arg Gln Leu
1               5                   10                  15

Val Gly Ile Ala Ala Ala Gln Pro Ala Met Ala Gln Val Gln Leu Val
            20                  25                  30

Glu Ser Trp Gly Gly Ser Val Gln Ala Gly Gly Ser Leu Arg Leu Ser
        35                  40                  45

Cys Thr Ala Pro Gly Phe Thr Ser Asn Ser Cys Arg Met Asp Trp Tyr
    50                  55                  60

Arg Gln Ala Ala Gly Lys Gln Arg Glu Trp Val Ser Ser Ile Ser Thr
65                  70                  75                  80

Asp Gly Arg Thr Ser Tyr Ala Asp Ser Val Lys Gly Arg Phe Thr Ile
                85                  90                  95

Ser Lys Asp Lys Ala Lys Asp Thr Val Tyr Leu Gln Met Asn Ser Leu
            100                 105                 110

Lys Pro Glu Asp Thr Ala Ile Tyr Tyr Cys Ala Val Arg Thr Asn Gly
        115                 120                 125

Tyr Arg Pro Gln Ser His Glu Phe Arg Tyr Trp Gly Pro Gly Thr Gln
    130                 135                 140

Val Thr Val Ser Ser Ala Ala Ala Ser Gly Ala Ala Ser Thr His His
145                 150                 155                 160
```

-continued

```
His His His His Ala Ser Thr Pro Gly Gly Ala Pro Val Pro Tyr Pro
                165                 170                 175

Asp Pro Leu Glu Pro Ala Ala Asn Ser His Pro Glu Thr Leu Val Lys
            180                 185                 190

Val Lys Asp Ala Glu Asp Gln Leu Gly Ala Arg Val Gly Tyr Ile Glu
        195                 200                 205

Leu Asp Leu Asn Ser Gly Lys Ile Leu Glu Ser Phe Arg Pro Glu Glu
    210                 215                 220

Arg Phe Pro Met Met Ser Thr Phe Lys Val Leu Leu Cys Gly Ala Val
225                 230                 235                 240

Leu Ser Arg Val Asp Ala Gly Gln Glu Gln Leu Gly Arg Arg Ile His
                245                 250                 255

Tyr Ser Gln Asn Asp Leu Val Glu Tyr Ser Pro Val Thr Glu Lys His
            260                 265                 270

Leu Thr Asp Gly Met Thr Val Arg Glu Leu Cys Ser Ala Ala Ile Thr
        275                 280                 285

Met Ser Asp Asn Thr Ala Ala Asn Leu Leu Leu Thr Thr Ile Gly Gly
    290                 295                 300

Pro Lys Glu Leu Thr Ala Phe Leu His Asn Met Gly Asp His Val Thr
305                 310                 315                 320

Arg Leu Asp Arg Trp Glu Pro Glu Leu Asn Glu Ala Ile Pro Asn Asp
                325                 330                 335

Glu Arg Asp Thr Thr Met Pro Ala Ala Met Ala Thr Thr Leu Arg Lys
            340                 345                 350

Leu Leu Thr Gly Glu Leu Leu Thr Leu Ala Ser Arg Gln Gln Leu Ile
        355                 360                 365

Asp Trp Met Glu Ala Asp Lys Val Ala Gly Pro Leu Leu Arg Ser Ala
    370                 375                 380

Leu Pro Ala Gly Trp Phe Ile Ala Asp Lys Ser Gly Ala Gly Glu Arg
385                 390                 395                 400

Gly Ser Arg Gly Ile Ile Ala Ala Leu Gly Pro Asp Gly Lys Pro Ser
                405                 410                 415

Arg Ile Val Val Ile Tyr Thr Thr Gly Ser Gln Ala Thr Met Asp Glu
            420                 425                 430

Arg Asn Arg Gln Ile Ala Glu Ile Gly Ala Ser Leu Ile Lys His Trp
        435                 440                 445
```

SYSTEMS, METHODS AND MICRORGANISMS FOR ANTIBODY PRODUCTION WITH TYPE III SECRETION SYSTEM

CROSS-REFERENCES TO RELATED APPLICATIONS

This application claims the benefit under 35 U.S.C. §371 to PCT/ES2008/070045 filed Mar. 12, 2008, which claims the benefit of Patent Application 200700644 filed Mar. 12, 2007 in Spain. The entire disclosures of both applications are incorporated by reference herein.

STATE OF THE ART

The possibility of expressing and selecting antibody molecules in bacteria, especially in *Escherichia coli* and its bacteriophages, has attracted the attention of biotechnology in recent decades and has enormously increased the biotechnological potential of antibodies for their use in diagnosis and therapy processes against various diseases, such as cancer or autoimmune diseases. The antibodies known as recombinant, produced in bacteria using genetic engineering techniques, are small fragments derived from the complete antibody molecules (e.g. IgGs) that retain the capacity to bind with the antigen. These antibody fragments preserve at least one of the variable domains (V) of immunoglobulins (Igs), where the antigen binding site resides, and can also include constant domain(s) (C) where other antibody functions reside (e.g. activation of the complement). Thus, although there are various formats of recombinant antibodies, they all have as a minimum common unit a V domain capable of antigen binding. In this way, on the basis of structural criteria, recombinant antibodies can be classified into at least three basic types: domain antibodies, (dAbs; if they only contain a V domain), single chain (Fv, scFv; if they contain the V domains of the heavy -VH- and light -VL- chains connected by means of a small flexible peptide) and Fab fragments (antigen binding fragment, Fab) formed by two polypeptide chains, one containing the domains VH-CH1 and the other domains VL-CL. Subsequently, through combinations of two, three or four (or more) of these basic units, whether dAbs, scFvs, or Fabs, diabodies, triabodies or tetrabodies can be obtained, which can provide molecules with more affinity (avidity) for the antigen due to having repetitive binding sites. Moreover, if different C domains are added to these molecules, a variety of recombinant antibody molecules, known collectively as minibodies, can be obtained. As previously stated, the different formats of recombinant antibodies contain at least one V domain capable of binding to a specific antigen.

The described dAb domain antibodies retain the capacity to bind to an antigen and include V domains derived from both "standard" natural antibodies (with heavy and light chains, such as those found in humans, mice, or rabbits) as well as natural antibodies with heavy chains only (or heavy chain antibodies), such as those produced by the family of camelids (e.g. camels, llamas and vicunas) or the IgNAR domains of shark species (e.g. nurse sharks). Hence, dAbs can include V domains of light chains (VL) or V domains of heavy chains (VH), whether of standard antibodies or heavy chain only antibodies (VHH, heavy chain only VH). Beneficial characteristics of dAb recombinant antibodies include their small size, low immunogenicity and rejection in humans, their ease of expression in bacteria and yeasts at high concentrations, and their biochemical properties of stability against denaturalizing agents and solubility.

Systems for injecting proteins from bacteria into eukaryotic cells, such as type III protein secretion systems (T3SS) can be used to deliver such dAb. T3SS are able to inject into the cytoplasm of a eukaryotic cell specific bacterial proteins. The natural proteins injected by T3SS systems, also known as effector proteins, are usually toxins that alter the metabolism of the eukaryotic cell. T3SSs are complex systems and comprise more than 20 different proteins that configure a molecular superstructure known as a needle complex or insectivore, which pierces the internal and external membranes of Gram negative bacteria forming a needle-shaped structure specialized in the secretion and injection of proteins. EPEC and EHEC strains the protein EscF, the protein EscC—which forms a hydrophilic channel in the external bacterial membrane—and the protein EscN, which is an essential ATPase for the secretion process located at the base of the needle. Other structural components of the EPEC and EHEC needle are the products of genes escR escS escT escU escD escJ escV and sepQ, among others. In addition to the needle complex, the injection of proteins into the eukaryotic cell via the T3SS system requires a group of proteins known as translocators which form a channel in the plasmatic membrane of the eukaryotic cell. These translocator proteins tend to be secreted by the T3SS themselves. In EPEC and EHEC strains, the translocator proteins are EspB and EspD. Also, in the T3SS of EPEC and EHEC, the protein EspA (also translocated by the T3SS) forms a filament that extends beyond the needle (EscF) to the translocation pore formed by EspB/D.

T3SS components are assembled sequentially; thus the first to assemble are the rings found in the internal and external membranes of the bacteria (EscV and EscC, internal and external respectively), between these two proteins a third one acts as a bridge (EscJ), in such a way that the protein that crosses the system has no contact with the periplasmic space. Then the needle proteins are assembled (EscF), the filaments of EspA and, finally, the translocator proteins EspD and EspB.

T3SS have been used to generate live vaccines based on attenuated bacterial strains. Thus, different antigens have been injected (bacterial, viral or tumoral) from attenuated bacterial strains (derived from *Salmonella enterica* or *Yersinia enterocolitica*) to induce an immune response in the host against the injected antigen/s. For example, attenuated strains of *Salmonella enterica* have been used for the injection of the Gag antigen of the HIV-1 virus or the tumoral antigen NY-ESO-1.

The EPEC and EHEC strains used in exemplary embodiments described herein are enteropathogens that develop an infection through a strong binding to the cells of the intestinal epithelium (enterocytes) known as the attaching and effacing A/E lesion. The capacity to bind intimately to the plasmatic membrane of the enterocytes is mediated by a bacterial adhesive called Intimin (eaeA), located in the bacteria's external membrane, which interacts with a receptor known as Tir (translocated intimin receptor) located in the plasmatic membrane of the epithelial cell and that the bacteria itself injects through the T3SS. The Intimin-Tir bonds facilitate the T3SS task of injecting effectors of the EPEC and EHEC strains towards the cytoplasm of the epithelial cell.

In EPEC and EHEC strains the genes that encode the structural components of the needle, the translocation pore, the intimin (eaeA) and Tir proteins, as well as most of the T3SS, are located in a genetic locus known as LEE (locus of enterocyte effacement) of 35 kb.

T3SS machinery recognizes signals present in the sequence of the effector proteins, or in the mRNAs encoding them, which are generically referred to as type III signal sequences (SS). These SS are only well-defined and empirically characterized in some of the T3SS effector proteins. In general, the SS tend to be located near the N-terminal end of the effector proteins, and are constituted of the first 15-30 amino acids of the effector protein, or of the first 15-30 codons of its mRNA. As a general rule, the SS do not demonstrate a consensus or identifiable motive. T3SS SS are not proteolysed following secretion, as occurs with other protein export signal sequences. In addition to the SS, some effector proteins depend on their interaction with specific T3SS chaperones for their secretion, known as class I chaperones. Nonetheless, it is worth mentioning that although an effector protein can depend on a class I chaperone for its secretion by the T3SS, the secretion of specific fusion proteins of the N-terminal SS of 15-30 amino acids with heterologous proteins (β-lactamase) does not depend on these chaperones. In natural effector proteins, the binding domains of class I chaperones are located immediately behind the N-terminal SS and are usually regions of approximately 50-100 amino acids. There are another two classes of T3SS chaperones (II and III) according to structural homologies, which take part in the stabilization and secretion of the different secreted proteins. Class II chaperones take part in the stabilization of translocator proteins (e.g. CesD is the chaperone of EspB and EspD in EPEC and EHEC). Class III chaperones take part in the secretion of some structural components of the needle (e.g. In EHEC and EPEC, CesA is the chaperone of EspA).

SUMMARY

Exemplary embodiments disclosed herein include a microorganism with a type III protein injection system (T3SS) useful for the extracellular secretion or injection of functionally active antibodies into eukaryotic cells, hereinafter microorganism T3SS, presenting a T3SS-Ab gene construct that comprises, at least, one DNA sequence containing the encoding sequence of the secretion signal region (SS) recognized by the T3SS system bonded, fused or linked to a DNA sequence that contains the encoding sequence of an antibody and that allows the expression of said functionally active fusion antibody (in one embodiment in its cytoplasm) and its secretion or injection outside.

Another exemplary embodiment disclosed herein includes a gene construct T3SS-Ab, hereinafter T3SS-Ab gene construct, which comprises, at least:

i) a DNA sequence encoding a type III secretion signal, and ii) a DNA sequence encoding an antibody of interest.

Another exemplary embodiment disclosed herein includes the T3SS-Ab gene construct, wherein the DNA sequence encoding a type III secretion signal (SS) is the SS sequence of *E. coli*, in one exemplary embodiment a fragment of the same, and in another exemplary embodiment SEQ ID NO: 5 which encodes the first 20 N-terminal amino acids of EspF (EspF20), where the type III secretion signal of its effector is located.

Another exemplary embodiment disclosed herein includes a gene expression vector, hereinafter expression vector T3SS-Ab, containing the T3SS-Ab gene construct, which allows the expression of said construct in the microorganism (in one embodiment in the microorganism's cytoplasm).

Another exemplary embodiment disclosed herein includes the fusion antibody T3SS-AB obtained through the expression of the gene construct or from the expression vector T3SS-Ab in the microorganism. A particular exemplary embodiment is constituted by the fusion antibody which comprises the SS signal sequence of sequence SEQ ID NO: 6.

Another exemplary embodiment disclosed herein includes a procedure for obtaining the microorganism, comprising the transfection or transformation of a microorganism with a type III secretion system (T3SS) using the gene construct or expression vector T3SS-Ab.

Another exemplary embodiment disclosed herein includes the use of the microorganism T3SS, in a biotechnology procedure of secretion and/or injection of functional recombinant antibodies of interest.

Another exemplary embodiment disclosed herein includes the use of the microorganism T3SS in a biotechnology procedure consisting of the production and extracellular secretion of a recombinant antibody (see Example 1).

Another exemplary embodiment disclosed herein includes use of the microorganism T3SS in the preparation of a medicine or therapeutic composition useful for treating diseases in humans, animals or plants.

Another exemplary embodiment disclosed herein includes a medicine or therapeutic composition useful for the treatment of diseases in humans, animals or plants, hereinafter medicine T3SS, which comprises the microorganism T3SS.

Finally, another exemplary embodiment disclosed herein includes the use of the T3SS medicine or therapeutic composition in a human or veterinary therapeutic procedure.

DETAILED DESCRIPTION

The system for injecting proteins into eukaryotic cells—type III secretion systems (T3SS)—present in pathogenic strains of *E. coli* and other Gram negative microorganisms (e.g. *Salmonella enterica, Pseudomonas aeruginosa*, etc.) described herein is surprisingly capable of efficiently secreting into the extracellular medium or of injecting active recombinant antibodies (capable of recognizing and binding to their antigen), in one embodiment dAbs and, in another embodiment $V_{HH}$, into the cytoplasm of a eukaryotic cell (in one embodiment human cells), and in particular embodiments the T3SS of EPEC and EHEC strains. This secretion or injection effect is achieved by fusion or linking of the antibodies with the secretion signal sequence that recognizes the secretion system (SS) of type III (T3SS: $EspF_{20}$, SEQ ID NO: 6), which does not prevent said antibodies from being functionally active once secreted (Example 1) or injected (Example 2). Using as a model enteropathogenic strains of *E. coli* carriers of these T3SS injection systems and dAbs from camel antibodies modified to contain the signal recognized by the bacterial injection machinery, it has been verified that the antibodies can be injected in active form into the cytoplasm of human cells HeLa and that they are capable of binding with an intracellular antigen present therein (Example 2). Also, this injection of functional antibodies from bacteria into a eukaryotic cell can be carried out without the transfer of any genetic material (DNA or RNA) as in the case of infection with modified viruses or through DNA or RNA transfer using physical or chemical methods.

As the system for injecting proteins from the bacteria into the eukaryotic cell, type III protein secretion systems were used (T3SS) and in this particular case the T3SS present in enteropathogenic (EPEC) and enterohaemorrhagic (EHEC) strains of *E. coli*. In this particular case the recombinant antibodies with the smallest known size (approx. 15 kDa) and formed by single V domain (domain antibodies dAb) were used. More specifically, the dAb recombinant antibodies selected as models are two $V_{HH}$ clones with reactivity to the green fluorescent protein GFP antigens (Vgfp clone) and a pig pancreatic enzyme α-amylase (Vamy clone), previously isolated by phage display and coming from gene libraries obtained from camels immunized with said antigens.

Thus, for the purpose of studying the possibilities of secretion and/or injection of the recombinant antibodies (domain, dAb) using the T3SS (of EPEC/EHEC) it was decided to fuse or link these antibodies to the SS sequences of the T3SS developing a gene construct. A well-characterized T3SS SS was used, which corresponds to the 20 N-terminal amino acids of the effector protein ($EspF_{20}$, SEQ ID NO: 6), present in a preserved manner in the EspF proteins of both EPEC and EHEC strains of *E. coli*. This SS had been identified through fusions of EspF to β-lactamase.

Therefore, one exemplary embodiment disclosed herein includes a microorganism with a type III protein injection system (T3SS) useful for the extracellular secretion or injection of functionally active antibodies into eukaryotic cells, hereinafter microorganism T3SS, which presents a T3SS-Ab gene construct that comprises at least one DNA sequence containing the sequence encoding the secretion signal region (SS) recognized by the T3SS system bound, fused or linked to a DNA sequence containing the sequence encoding an antibody and that allows the expression of said functionally active fusion antibody (in one embodiment in its cytoplasm) and its secretion or injection outside.

As used herein, the term "microorganism" refers to any natural, pathogenic or non-pathogenic bacteria, including attenuated, commensal, probiotic, environmental strains, etc., isolated in nature or any bacterial strain or species with any type of genetic modification, whether derived from pathogenic or non-pathogenic strains, attenuated, commensal, probiotic, environmental strains, etc, and whether they are isolated modifications through natural selections, random or directed mutagenesis processes, or recombinant DNA techniques, in one exemplary embodiment a Gram negative microorganism, presenting a type III protein secretion system (T3SS) belonging, by way of illustration without limiting the scope of embodiments disclosed herein, to the following group: *E. coli, Salmonella enterica, Pseudomonas aeruginosa, Yersinia pseudotuberculosis, Yersinia pestis, Shigella flexnerii, Citrobacter rodentium, Pseudomonas syringae, Ralstonia solanacearum, Xanthomonas campestres* and *Erwinia amylovora.*

The type III protein secretion system, as referred to herein, includes both a wild or a natural system, or any other modified or artificially selected using any technique based on the latter. The modified T3SS system can contain mutations in one or several components, whether these are produced spontaneously or through in vitro or in vivo mutagenesis, and can also be a T3SS formed by the expression of components obtained from different strains and/or bacterial species.

As used herein, the term "eukaryotic cell" refers to any eukaryotic cell coming from an animal, plant, fungi, yeasts and protozoa; with any cellular lineage (without limitation, epithelial cells, endothelial, fibroblasts, muscle cells, neuronal cells, glial, lymphoid and other blood cells such as erythrocytes, monocytes, macrophages, neutrophils, eosynophils, basophils or antigen-presenter cells as well as dendritic cells, M-cells, etc.) in addition to stem cells whether embryonic or from adult organisms.

As used herein, the term "secretion signal recognized by the T3SS system", is a fragment of protein (peptide) or RNA of a natural effector of T3SS, or the complete molecule of RNA or protein of a T3SS effector, or fragment of protein or RNA, or a complete molecule, obtained through recombinant DNA or chemical synthesis and that has demonstrated the capacity to be recognized by any T3SS as a secretion signal.

As used herein, the term "functionally active antibody" refers to a recombinant antibody or miniantibody that retains its capacity to bind to a pertinent antigen, defined as fragments derived from antibodies constructed using recombinant DNA technology that, despite their smaller size, retain their capacity to bind to the antigen since they retain at least one variable domain of immunoglobulin where the antigen-binding zones reside, and belonging, by way of illustration without limiting the scope of exemplary embodiments disclosed herein, to the following group: Fab, F(ab')2, scFv, and single-domain recombinant antibodies (dAbs). In the context of exemplary embodiments disclosed herein, single-domain and/or immunoglobulin-type domain recombinant antibodies with independent binding and recognition capacities are understood to mean both the variable domains of heavy chains, (VH), the variable domains of light chains (VL), the recombinant antibodies of camelids (VHH), the recombinant antibodies of humanized camelids, the recombinant antibodies of other camelised species, the single-domain IgNAR antibodies of cartilaginous fish; in other words, it includes both domains which are naturally single-domain (as in the case of VHH and IgNAR), as well as antibodies which have been altered through engineering so that they are on their own capable of interacting with the antigen and of improving their stability and solubility properties. This definition includes any modification of the recombinant antibodies such as their multimerization or fusion to any molecule (e.g. toxins, enzymes, antigens, other antibody fragments, etc.).

The functionally active antibody can be obtained from a human being or an animal (without limitation, camels, llamas, vicuñas, mice, rats, rabbits, horses, nurse sharks, etc.) or through recombinant DNA techniques or the chemical synthesis of genes, or through the in vitro or in vivo selection of antibody gene libraries, using any strain of *Escherichia coli*, pathogenic or non-pathogenic, or any other strain or bacterial species containing a T3SS of any origin and using any recognized signal said T3SS to any eukaryotic cell.

Therefore, exemplary embodiments disclosed herein include a microorganism wherein the microorganism is a bacterium, in one exemplary embodiment a Gram negative non-pathogenic or attenuated bacterium.

According to another exemplary embodiment disclosed herein the Gram negative bacteria is a non-pathogenic or attenuated bacteria from animals belonging, by way of non-limiting illustration, to the following group: *E. coli, Salmonella enterica, Yersinia pseudotuberculosis, Yersinia pestis, Pseudomonas aeruginosa, Shigella flexnerii* and *Citrobacter rodentium*) or from plants, belonging, by way of illustration, to the following group: *Pseudomonas syringae, Ralstonia solanacearum, Xanthomonas campestres* and *Erwinia amylovora.*

Another exemplary embodiment disclosed herein includes the enteropathogenic (EPEC) and enterohaemorrhagic (EHEC) strain of *E. coli*, wherein the DNA T3SS-Ab gene construct comprises a DNA sequence encoding T3SS of SEQ ID NO: 5 and wherein the DNA sequence encoding the antibody is a single-domain antibody dAb, in one exemplary embodiment of type $V_{HH}$. A specific exemplary embodiment includes a microorganism, by way of illustration and without limitation, belonging to the following group: strains EPEC O127:H6 and EHEC O157:H7 (see Example 1 and 2).

Another exemplary embodiment disclosed herein includes the gene construct T3SS-Ab, hereinafter T3SS-Ab gene construct, which comprises, at least:

iii) a DNA sequence encoding a type III secretion signal, and iv) a DNA sequence encoding an antibody of interest.

The DNA sequence encoding a type III secretion signal (SS) used in the T3SS-Ab gene construct can be constituted by the DNA sequence encoding the secretion signal sequence (SS) of *E. coli* or a fragment of said sequence, or an analogous DNA sequence, or a sequence of nucleotides encoding a variant, natural or artificial of SS or a fragment of same that comprises the abovementioned minimum domain to be recognized and secreted/injected by the T3SS machinery. As previously discussed, the SS are usually located near the N-terminal end of the effector proteins, and consist of the first 15-30 amino acids of the effector protein, or the first 15-30 codons of its mRNA.

In the sense used in this description, the term “analogous” seeks to include any sequence of nucleotides that can be isolated or constructed based on the DNA sequences disclosed herein, for example, through the introduction of conservative or non-conservative replacements of nucleotides, including the insertion of one or more nucleotides, the addition of one or more nucleotides to any end of the molecule or the deletion of one or more nucleotides from any end or inside the sequence, and encoding a peptide or protein with similar activity to the original, in other words a type III secretion signal (SS).

In general, an analogous DNA sequence is substantially homologous to the sequence of nucleotides described above. In the sense used in this description, the expression “substantially homologous” means that the sequences of nucleotides in question have a degree of similarity of, at least 40%, in one exemplary embodiment, at least 85%, or in another exemplary embodiment, at least 95%.

At the same time, the DNA sequence encoding a type III secretion signal (SS), as an element of the T3SS-Ab gene construct, can be linked or fused to any point of the sequence encoding a recombinant antibody (ends 5' or 3' of the DNA or RNA, as well as any internal sequence).

Another exemplary embodiment disclosed herein includes the DNA sequence encoding said fusion antibody that can be constructed in this sense or inversely, with or without additional sequences of DNA. The T3SS-Ab gene construct can also contain, if necessary and to allow improved isolation or detection of the fusion antibody of interest, a sequence of DNA encoding a peptide that can be used for the purposes or isolation or detection of said protein. Therefore, another exemplary embodiment disclosed herein includes any DNA sequence encoding a peptide or peptidic sequence that allows the isolation or detection of the T3SS fusion antibody, for example, by way of illustration and without limiting the scope of exemplary embodiments disclosed herein, a sequence of polyhistidine (6×His), a peptidic sequence recognizable by a monoclonal antibody (for example, E-tag for its identification, or any other that serves to purify the resulting fusion protein through immunoaffinity chromatography: label peptides such as c-myc, HA, FLAG) (Using antibodies: a laboratory manual. Ed. Harlow and David Lane (1999). Cold Spring Harbor Laboratory Press. New York. Chapter: Tagging proteins. Pp. 347-377).

Another exemplary embodiment disclosed herein includes the T3SS-Ab gene construct wherein the DNA sequence encoding a type III secretion signal (SS) is the SS sequence of *E. coli*, in one exemplary embodiment a fragment of same, and in another exemplary embodiment SEQ ID NO: 5 which encodes the first 20 N-terminal amino acids of EspF (EspF20), where the type III secretion signal of its effector is found.

Another exemplary embodiment disclosed herein includes a T3SS-Ab gene construct wherein the sequence encoding a functionally active antibody comprises a camel antibody, and in one exemplary embodiment a gene construct of SEQ ID NO: 2 and NO4 (see example 1 and 2).

Another exemplary embodiment disclosed herein includes a T3SS-Ab gene construct containing a linker sequence or binding sequence between the sequences encoding for the SS sequence and the antibody sequence, that can include, if wanted, a sequence of DNA encoding a sequence of amino acids that can be specifically split by enzymatic or chemical means with a view to liberating the fusion antibody. In this case, the T3SS-Ab gene construct can include a DNA sequence encoding a sequence of amino acids capable of being split specifically by enzymatic or chemical means. In a particular embodiment said sequence comprises a sequence of nucleotides encoding a protease cleavage recognition site, for example, an enterokinase, Arg-C endoprotease, Glu-C endoprotease, Lys-C endoprotease, coagulation factor Xa and such like. In another particular embodiment, said DNA sequence comprises a DNA sequence encoding a site that can be split specifically by a chemical reagent such as, for example, cyanogen bromide which splits residues of methionine or any other suitable chemical reagent.

The T3SS-Ab gene construct can be obtained by one of ordinary skill in the art through the use of well-known techniques in the state of the art (Sambrook et al. “Molecular cloning, a Laboratory Manual 2nd ed., Cold Spring Harbor Laboratory Press, N.Y., 1989 vol 1-3). Said DNA gene construct can be integrated in an expression vector that allows the expression of the DNA sequence encoding the fusion antibody to be regulated in appropriate conditions.

Therefore, another exemplary embodiment disclosed herein includes a gene expression vector, hereinafter expression vector T3SS-Ab, containing the T3SS-Ab gene construct and that allows the expression of said construct in the cytoplasm of the microorganism.

In general, the expression vector T3SS-Ab comprises, at least the DNA sequence T3SS-Ab, at least, one promoter that directs its transcription (pT7, plac, ptrc, ptac, pBAD, ptet, etc), to which it is operatively linked, and other necessary or appropriate sequences that control and regulate the transcription of the gene and, where applicable, the translation of the product of interest, for example, transcription start and stop signals (tlt2, etc), polyadenylation signal, origin of replication, ribosome binding sequences (RBS), sequences encoding transcriptional regulators (enhancers), transcriptional silencers (silencers), repressors, etc. Examples of suitable expression vectors can be selected according to the conditions and needs of each specific case from among expression plasmids of microorganisms, which can additionally contain markers that can be used to select the cells transfected or transformed with the gene or genes of interest. The choice of vector will depend on the host cell and the type of use required. Therefore, according to a particular exemplary embodiment, said vector is a plasmid. Said vector can be obtained using conventional methods known by technicians in the field and in the same way different methods can be used for the transformation of microorganisms—chemical transformation, electroporation, microinjection, etc.—as described in various manuals [Sambrook, J., Fritsch, E. F., and Maniatis, T. (1989). Molecular cloning: a laboratory manual, 2nd ed. Cold Spring Harbor Laboratory, Cold Spring Harbor, N.Y.]. In addition to plasmids, other vectors can be used such as bacteriophages, in phagemids, cosmids, artificial chromosomes or integrated in any point of the chromosome or chromosomes.

Another exemplary embodiment disclosed herein includes a T3SS-Ab expression vector wherein the vector is a plasmid comprising as SS sequence SEQ ID NO: 5, and as recombinant antibody sequence, a sequence of a camel antibody. Another particular embodiment is presented by a plasmid such as for example plasmids pEspFVamy and pEspFVgfp (see Example 1 and 2).

Another exemplary embodiment disclosed herein includes the T3SS-AB fusion antibody obtained through the expression of the gene construct or from the T3SS-Ab expression vector in the microorganism. A particular exemplary embodiment is constituted by the fusion antibody comprising the SS signal sequence of sequence SEQ ID NO: 6.

Another exemplary embodiment disclosed herein includes the use of the gene construct and the T3SS-Ab expression vector for obtaining the microorganism.

Thus, another exemplary embodiment disclosed herein includes a procedure for obtaining the microorganism, which comprises the transfection or transformation of a microorganism with a type III secretion system (T3SS) using the T3SS-Ab gene construct or expression vector.

Exemplary embodiments described herein allow these bacterial strains to be used as production factories of recombinant antibodies that can be secreted into the extracellular medium without the need for cell lysis and subsequently purified. Likewise, these microorganisms can be used therapeutically, in such a way that non-pathogenic or attenuated bacterial strains of pathogens (e.g. of *E. coli* or *Salmonella* or *Yersinia*) but carriers of the protein injection and secretion systems, allow secretion into the medium or injection into the target human eukaryotic cells of recombinant antibodies that regulate the action of extracellular elements or the cell metabolism or some type of cell process, by inhibiting or activating signal cascades or transcription factors (e.g. by disactivating enzymes or proteins involved in pathologies). Some diseases and cell processes that could be the object of treatment with this therapy include, without limitation: tumoral angiogenesis, cancer, inflammatory processes, immune deficiency and transplants, and viral, bacterial, and fungal infections.

Another exemplary embodiment disclosed herein includes the use of the microorganism T3SS, use of the microorganism, in a biotechnology process of secretion and/or injection of functional recombinant antibodies of interest.

Secretion of the T3SS antibody into the extracellular medium on the part of the T3SS microorganism can be carried out directly into the cultivation medium where it is grown in vitro for subsequent use of the supernatant or purification of the antibody from it, or directly into the encountered medium when it is inside a live being, whether animal, in one exemplary embodiment a human being, or a plant.

Another exemplary embodiment disclosed herein includes the use of the T3SS microorganism in a biotechnology process that consists of the production and extracellular secretion of a recombinant antibody (see Example 1). According to a particular exemplary embodiment, by way of illustration and without limitation, the recombinant antibody belongs to the following group: Fab, F(ab')2, scFv, and single-domain recombinant antibodies, (dAbs), in one exemplary embodiment dAbs, and in another exemplary embodiment $V_{HH}$ of camels.

These antibodies can be used in different industrial sectors such as human and veterinary health (diagnosis and therapy), in biotechnology processes, in the agrifood sector, bioremediation, chemical synthesis, etc.

The antibody T3SS can be used directly or following purification of the antibody from the supernatant, using various systems.

In the case of using the microorganism per se as a therapeutic compound for human or veterinary diseases, and prior to its administration, it must be prepared as a pharmaceutical or food composition (probiotic strain) in the appropriate manner. In this regard, it could form part (on its own or in combination with other microorganisms, including probiotics) (Combination of probiotics EP1359816 Valio Ltd). Also, it can be included in pharmaceutical preparations in the form of capsules (Micro-encapsulated lactobacilli for medical applications WO 96/38159), in lyophilised, liquid form, in pills or gels.

Therefore, another exemplary embodiment disclosed herein includes the use of the microorganism T3SS in the preparation of a medicine or therapeutic composition useful for treating diseases in humans, animals or plants.

In this sense, another exemplary embodiment disclosed herein includes a medicine or therapeutic composition useful for the treatment of diseases in humans, animals, or plants, hereinafter medicine T3SS, which comprises the microorganism T3SS.

A particular object is constituted by a medicine T3SS that is useful for treating diseases in humans belonging, by way of illustration and without limitation, to the following group: tumoral angiogenesis, cancer, inflammatory processes, immune deficiency and transplants, and viral, bacterial and fungal infections.

Finally, another exemplary embodiment disclosed herein includes the use of the medicine or therapeutic composition T3SS in a human or veterinary therapeutic procedure.

EXAMPLES

Example 1

Figure 1:
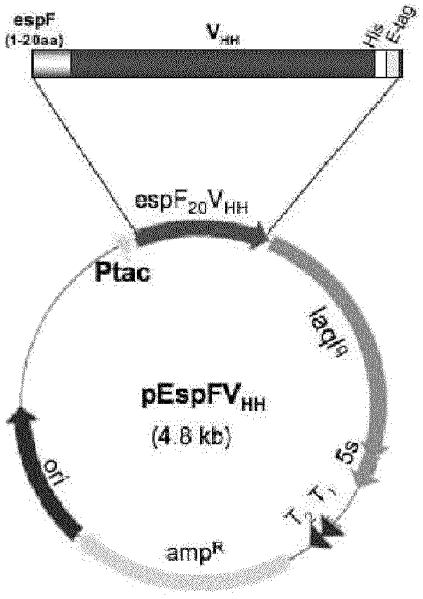
FIG. 1. Diagram of the plasmids used for translocation by the T3SS. The $V_{HH}$ antibodies are fused to the $EspF_{20}$ signal on the N-terminal end and to the epitopes 6×His and E-tag on the C-terminal end.

Secretion of the Functionally Active Fusion Antibody (EspF-$V_{HH}$) into the Extracellular Medium is Dependent on T3SS Two plasmids, called pEspFVamy and pEspFVgfp, were constructed derived from vector pSA10 with fusions encoding the first 20 N-terminal amino acids EspF ($EspF_{20}$), which are the type III secretion signal of this effector (SEQ ID NO: 6), and the camel bodies $V_{HH}$ anti-amylase (Vamy) and anti-GFP (Vgfp) (FIG. 1; SEQ ID NO: 1 to 4). Also, epitopes 6×his and E-tag were included on the C-terminal end of these fusions in order to facilitate immunodetection and purification of the proteins (SEQ ID NO: 2 and SEQ ID NO: 4, respectively).

Figure 2:
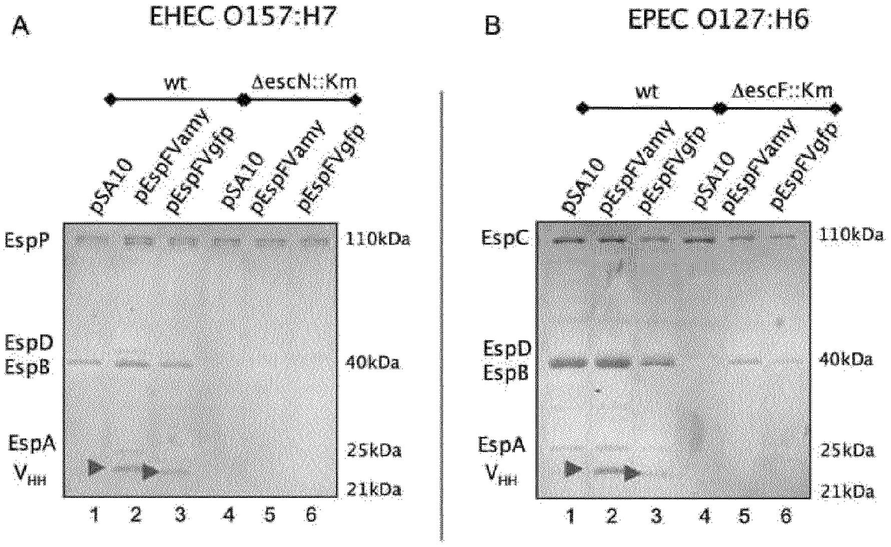
FIG. 2. Secretion through T3SS of $V_{HH}$s into the extracellular medium in EHEC and EPEC. Supernatants from the induction in DMEM (Bulbecco's modified Eagle's medium) of the *E. coli* EHEC (A) and EPEC (B) strains, wild and mutant in the T3SS, carrying the indicated plasmids in each lane. The proteins present in the supernatants were precipitated with TCA (trichloroacetic) and analyzed by SDS-PAGE and by staining with Coomassie blue. Red arrow tips indicate the fusion antibody.

Plasmids pEspFVamy and pEspFVgfp were used to transform strains EPEC O127:H6 and EHEC O157:H7 (Table 1). The same strains were transformed with the empty vector pSA10, as a control. Bacteria from these strains containing these plasmids were grown in DMEM medium at 37° C., which artificially activates the T3SS, and expression was induced of the fusions with IPTG (Isopropyl β-D-1-thiogalactopyranoside) during 3.5 hours (this time proved to be optimum in preliminary experiments with inductions lasting from 1 to 16 hours). Subsequently, the proteins present in the supernatants were analyzed using SDS-PAGE and by staining with Coomassie blue. The presence of protein bands of approx. 22-23 kDa (Kilodalton) was observed in the supernatants of the cultures, which could correspond to both $V_{HH}$ antibodies fused to the N-terminal signal $EspF_{20}$ and the C-terminal epitopes 6×his and E-tag (FIGS. 2A and 2B, lanes 2 and 3; red arrows). These bands did not appear in the supernatants of the strains with the vector pSA10 (FIGS. 2A and 2B, lane 1), where other secreted proteins did appear (e.g. EspC/P, EspB, EspD, EspA).

To demonstrate that the secretion of the fusion antibodies EspF-$V_{HH}$ was produced by the T3SS, defective mutant strains were transformed in the T3SS, EHEC DescN::Km and EPEC DescF::Km, (see Garmendia (Cell Microbiol 6, 1167-1183 (2004)) and Wilson (Cell Microbiol 3, 753-762 (2001)) both of which are incorporated by reference for their teachings regarding the same) with the plasmids pSA10, pEspF-Vamy and pEspFVgfp. After induction with IPTG in conditions identical to those for the wild strain, the proteins present in the supernatants were analyzed and the absence of the proteins secreted by T3SS was observed (e.g. EspD, EspB, EspA) as well as of the fusion antibodies EspF-$V_{HH}$ (FIGS. 2A and 2B, lanes 4 to 6). As a control, the secretion of the proteins EspC or EspP (secreted by the type V secretion system) was not affected by these mutation DescF or DescN (FIGS. 2A and 2B).

In order to identify the secreted fusion antibodies $EspF_{20}$-$V_{HH}$ unequivocally, advantage was taken of the fact that both contain on the C-terminal end an E epitope specifically recognized by a monoclonal antibody (mAb) anti-E-tag. The proteins present in the supernatants of the abovementioned cultures, of wild EPEC and EHEC strains, as well as of their mutants ΔescN or ΔescF, were analyzed by SDS-PAGE and Western blot developed with the mAb anti-E-tag conjugated to peroxide (POD) (FIG. 3A).

Figure 3:
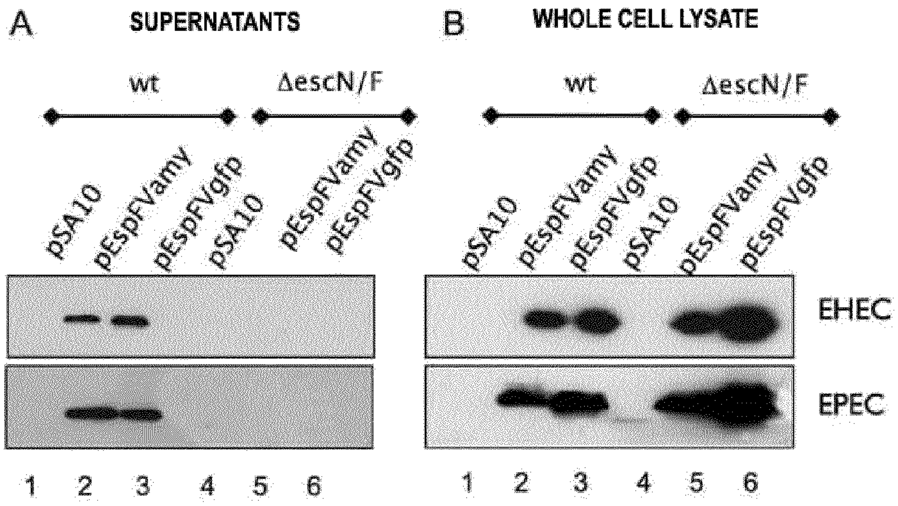
FIG. 3. Immunodetection of $V_{HH}$s in EHEC and EPEC. (A) Supernatants and (B) whole cell lysates from induction in the DMEM medium of the EPEC and EHEC strains of *E. coli*, wild and mutant for T3SS, carrying the plasmids indicated in each lane, analyzed using Western blot developed with the monoclonal antibody anti-Etag-POD (anti-Etag-peroxidase).

It can be observed that in the supernatants of the wild strains of EPEC and EHEC both fusion antibodies EspF-$V_{HH}$ are detected with the mAb anti-E-tag-POD (FIG. 3A, lanes 2 and 3) whereas these proteins are not detected in the supernatants of the mutant strains ΔescN or ΔescF (FIG. 3A, lanes 5 and 6). As a control, one can appreciate that these bands do not appear in the supernatants of the wild strains transformed with pSA10 (FIG. 3A, lane 1). At the same time, upon analysis with SDS-PAGE and Western blot with anti-E-tag mAb-POD of the whole cell lysates of these cultures it was observed that both EspF-$V_{HH}$ fusions occurred intracellularly in both wild and mutant strains ΔescN or ΔescF (FIG. 3B), and even an increase of intracellular accumulation can be appreciated in the mutants. These results indicate that the EspF-$V_{HH}$ fusion antibodies are only secreted into the extracellular medium in the presence of a functional T3SS.

Figure 4:
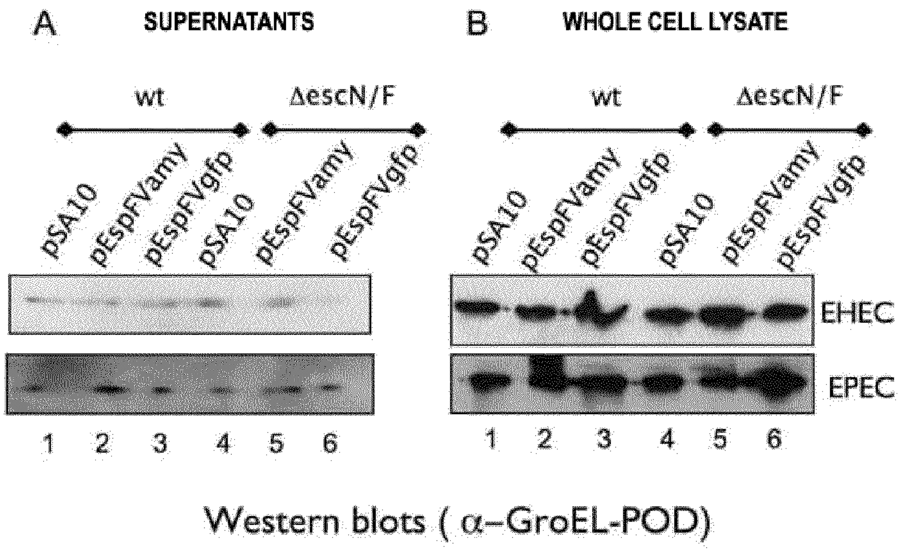
FIG. 4. Absence of lysis of EPEC and EHEC following induction of the $V_{HH}$. (A) Supernatants and Whole cell lysates from the induction in DMEM of the EPEC and EHEC strains of *E. coli*, wild and mutant for type III secretion, carrying the plasmids indicated in each lane, analyzed using Western blot developed with the monoclonal antibody anti-GroEL-POD.

In order to discard the possibility that a higher cell lysis of the cultures that express the fusion proteins EspF-$V_{HH}$ in strains containing an active T3SS could explain the appearance of the antibodies in the extracellular medium, a lysis control was carried out, which detected the presence of the major cytoplasmic chaperone GroEL in the supernatants of the cultures. Through Western blot with mAb anti-GroEL-POD (FIG. 4) it was verified that GroEL was only detectable at very low levels in the supernatants of the cultures (FIG. 4A). Moreover, the concentration of GroEL did not vary between the strains EPEC or EHEC wild and mutant ΔescN or ΔescF expressing the fusion proteins EspF-$V_{HH}$, nor in relation to the levels found in these strains with the empty vector pSA10 (FIG. 4A, lanes 1 and 4). The intracellular levels of GroEL are equally homogenous in all strains and irrespective of the plasmids that they contain (FIG. 4B). Therefore, the expression of the EspF-$V_{HH}$ fusions does not induce a cell lysis that justifies its presence in supernatants of the wild EPEC or EHEC strains with an active T3SS.

Figure 5:
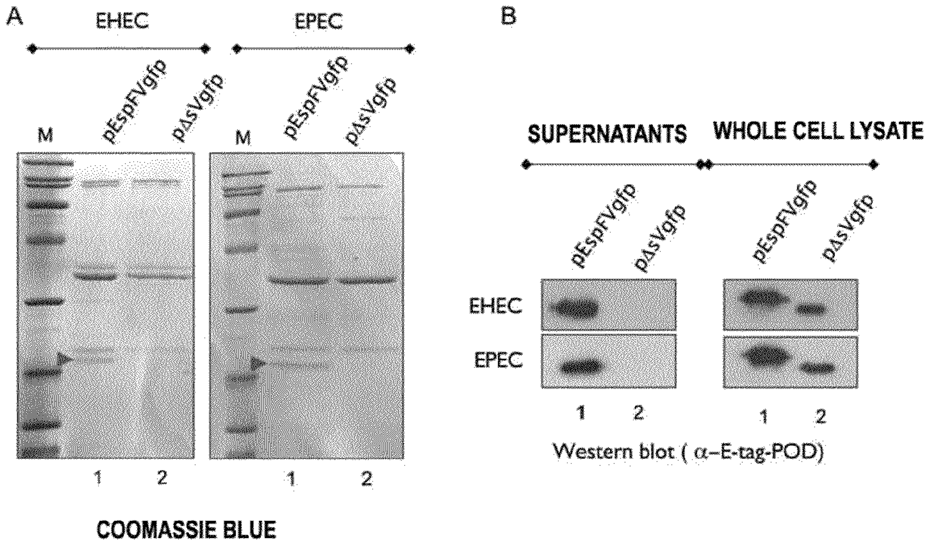
FIG. 5. The secretion of $V_{HH}$ depends on the type III signal $EspF_{20}$. Comparison of the protein secreted in EHEC and EPEC strains with the plasmids pEspF-Vgfp and pΔsVgfp. (A) SDS-PAGE of supernatants precipitated with TCA stained with Coomassie blue. (B) Western blot with mAb anti-E-tag-POD of Supernatants and Whole cell lysates.

In order to confirm that the fusions of antibodies EspF-$V_{HH}$ were secreted in a manner dependent on the $EsP_{20}$ signal this sequence was eliminated from the plasmid pEspF-Vgfp constructing the derivative pΔsVgfp with the sequence ΔsVgfp (SEQ ID NO: 7 and 8). Both plasmids were used to transform wild EPEC and EHEC strains and the proteins present in the supernatants of the cultures were analyzed following induction with IPTG. As one can observe from FIG. 5, the band corresponding to the antibody Vgfp can be detected in both staining with Coomassie (FIG. 5A) and in Western blot with anti-E-tag-POD (FIG. 5B) in the supernatants of the EPEC and EHEC strains transformed with pEspF-Vgfp, but not in those transformed with pΔsVgfp. The intracellular production of the protein without signal EspF was detected with anti-E-tag-POD in the whole cell lysates containing pΔsVgfp (FIG. 5B). Therefore, the sequence $EspF_{20}$ is necessary for the secretion of the fusion proteins EspF-$V_{HH}$ in both EPEC and EHEC strains. Due to the identical behavior of EHEC and EPEC strains in the secretion of the fusion antibodies EspF-$V_{HH}$ by the T3SS, the following experiments were carried out using EPEC strains unless otherwise indicated.

Figure 6:
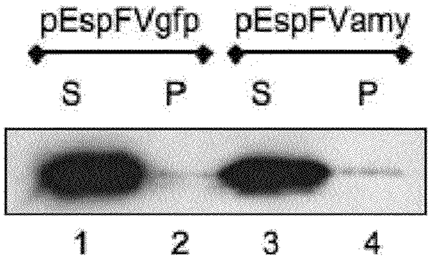
FIG. 6. Solubility of the EspF-VHH fusions. The supernatants of the cultures after induction were ultra-centrifuged (100,000×g) and Western blot with mAb anti-E-tag-POD was used to analyze the presence of the EspF-$V_{HH}$ fusions in the resulting supernatants (S) and pellet (P).

To confirm that the fusion antibodies EspF-$V_{HH}$ secreted into the medium were soluble and not associated to membrane vesicles or forming any type of protein aggregation, the supernatants of EPEC cultures containing fusion proteins EspF-Vamy and EspF-Vgfp were centrifuged at high speed (100,000×g, 1 hour). After centrifugation, the proteins present in the supernatants (S) and the pellets (P) were analyzed using SDS-PAGE and Western blot with anti-E-tag-POD (FIG. 6). In these experiments, it was observed that almost the whole secreted protein corresponding to both EspF-$V_{HH}$ fusions was soluble after centrifugation, indicating that it was not aggregated nor did it form part of membrane vesicles.

Figure 7:
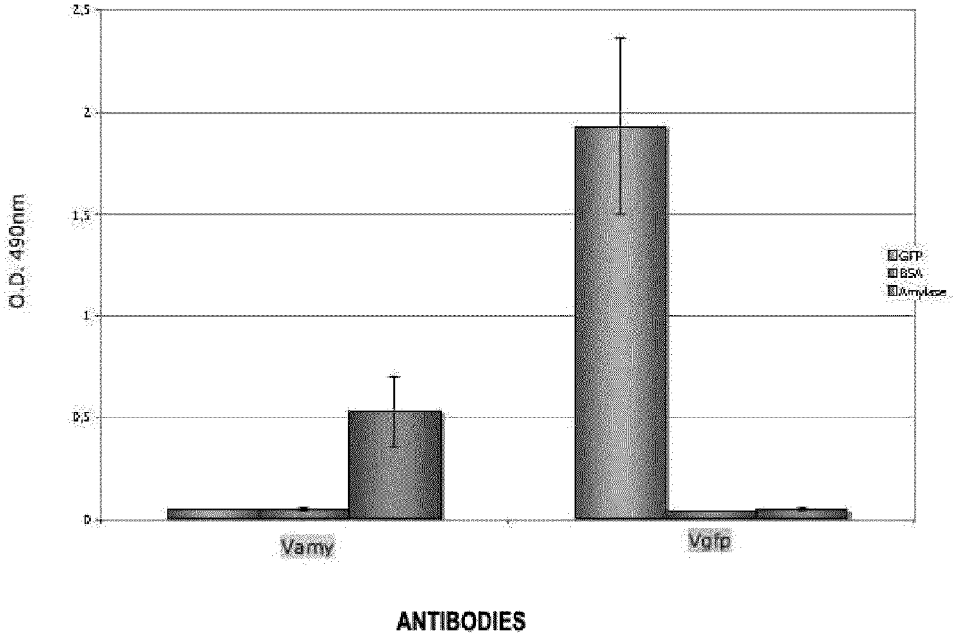
FIG. 7. Activity of the $V_{HH}$ antibodies secreted by the T3SS. ELISA (Enzyme-Linked ImmunoSorbent Assay) test showing the binding data of the $V_{HH}$ anti-amylase (Vamy) and anti-GFP (Vgfp) against the antigens GFP (green), α-amylase (orange) and BSA (blue). The ELISA was developed with mAb anti-E-tag-POD and Absorbance was measured at 490 nm (OD 490 nm).

The main characteristic of an antibody is its capacity to bind to an antigen in a specific manner. In order to check that this characteristic was retained in the secreted fusion antibodies EspF-$V_{HH}$, ELISA tests were carried out on the supernatants of the cultures of EPEC strains transformed with the plasmids pEspFVamy or pEspFVgfp. The tests used the supernatants obtained following induction and these were added to plates covered with the antigens of each of these fusion antibodies (α-amylase and GFP) as well as to a negative control antigen for both (BSA (Bovine serum albúmina)). Following several washes with PBS (Phosphate buffered saline), the binding of the fusion antibodies EspF-$V_{HH}$ to the antigens was developed with the mAb anti-E-tag conjugated with peroxidase. As one can appreciate from FIG. 7, a specific binding was observed of each fusion antibody (EspF-Vamy and EspF-Vgfp) to its corresponding antigen (α-amylase and GFP) and in no case was reactivity of the fusions to other antigens observed (FIG. 7).

Similar experiments were carried out with the EHEC strain and it was possible to verify this same result. Therefore, the binding of the fusion antibodies EspF-$V_{HH}$ to the antigens confirmed that the antibodies secreted by the T3SS system of EPEC and EHEC were functionally active. In these experiments it was also observed that the supernatants containing the fusion antibody EspF-Vgfp produced always higher ELISA signals (to GFP) than those that contained EspF-Vamy (against α-amylase), despite the fact that the levels of both fusions in the supernatants were very similar (see FIG. 2). This is due to the different affinity of these antibodies for their antigens (see below).

Figure 8:
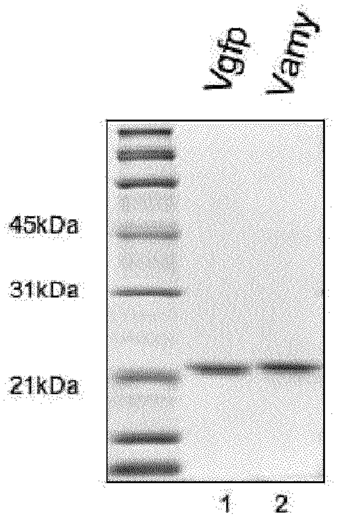
FIG. 8. EspF-VHH fusions purified after T3SS secretion. Staining with Coomassie blue of the purified proteins EspF-Vgfp (lane 1) and EspF-Vgfp (lane 2) following metal-affinity chromatography analyzed by SDS-PAGE.

The placing on the C-terminal end of the epitope 6×his offered the possibility of purifying the fusion antibodies EspF-$V_{HH}$ in the supernatants by means of metal affinity resin chromatography (e.g. cobalt). Following this step of chromatography, both fusion antibodies were obtained with a purity of >95% as developed by the analysis using SDS-PAGE and staining with Coomassie blue (FIG. 8).

Figure 9:
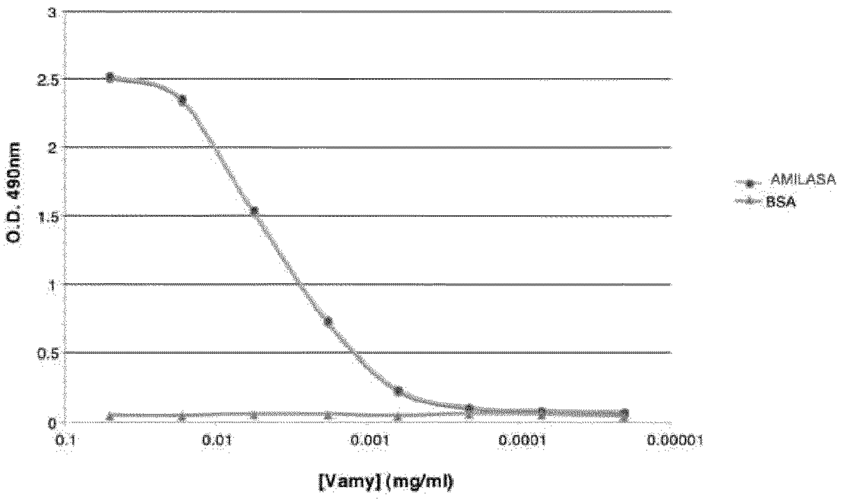
FIG. 9. Binding curves to the antigens α-amylase and bovine albumin (BSA) of the purified EspF-Vamy fusion. The curve was drawn using the values of Absorbance at 490 nm (OD 490 nm) obtained from ELISA tests with both antigens and at the specified concentrations of the EspF-Vamy fusion.
Figure 10:
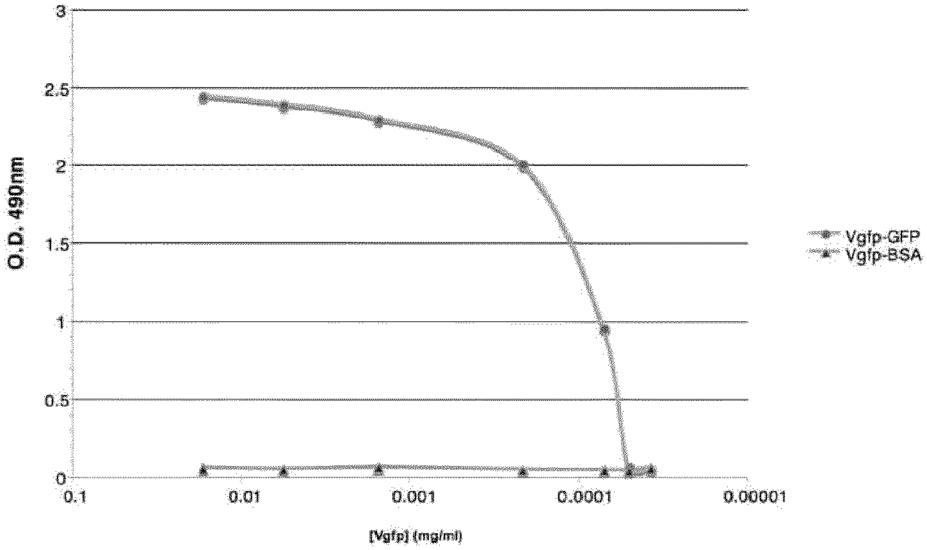
FIG. 10. Binding curves to the antigens GFP (Green Fluorescent Protein) and bovine albumin (BSA) of the purified EspF-Vgfp fusion. The curve was drawn using the values of Absorbance at 490 nm (OD 490 nm) obtained from ELISA tests with both antigens and at the specified concentrations of EspF-Vgfp fusion.

Next ELISA tests were carried out against GFP and α-amylase with different concentrations of the fusion antibodies EspF-$V_{HH}$, in order to obtain the binding curves of these antibodies to their corresponding antigens. As can be observed from FIGS. 9 and 10, characteristic curves were obtained of a specific binding of each antibody to its corresponding antigen, with the EspF-Vgfp fusion displaying more affinity than the EspF-Vamy fusion.

Example 2

Injection into Eukaryotic Cells of EspF-$V_{HH}$ Fusions with β-Lactamase

In order to obtain evidence of whether the fusion antibodies EspF-$V_{HH}$ could be translocated with the T3SS from bacteria to the cytoplasm of a eukaryotic cell, initially a test was carried out based on the catalytic activity of the β-lactamase enzyme, absent from eukaryotic cells. It had been described that the β-lactamase enzyme, lacking its natural signal peptide, could be translocated from the cytoplasm of wild EPEC strains to the cytoplasm of the eukaryotic cell. To do so, the T3SS secretion signal (SS) was used, as $EspF_{20}$, fused to the N-terminal end of β-lactamase. The translocated fusions (e.g. $EspF_{20}$-β-lactamase) were easily detectable in the cytoplasm of the eukaryotic cell thanks to the use of a fluorescent substrate of β-lactamase (CCF2/AM; see materials and methods) which can be added to cells in culture and that passes from emitting green to blue if it is degraded by the enzyme.

Figure 11:
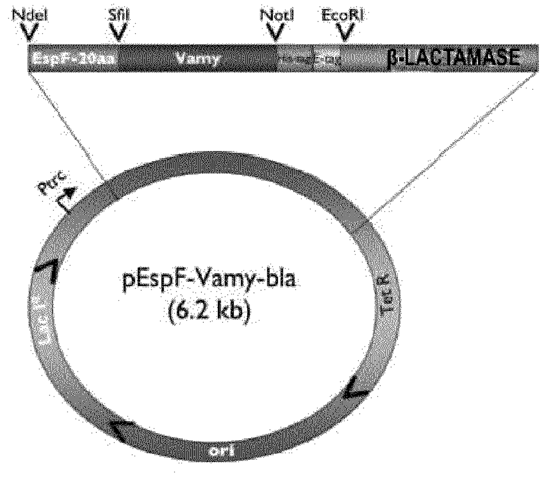
FIG. 11. Drawing of the pEspF-Vamy-bla plasmid, derivative of pCX340, which expresses under the control of the promoter Ptrc the fusion of EspF20-Vamy with the epitopes 6×his (6× Histidines aminoacids), E-tag and β-lactamase. The most important restriction sites are shown.

For these tests, the vector pCX340 was used, which encodes β-lactamase under the control of the promoter Ptrc inducible by IPTG (FIG. 11). Two derivatives of pCX340 were constructed wherein on the N-terminal end of the β-lactamase the $EspF_{20}$-Vamy fusion was bound (pEspF-Vamy-bla: SEQ ID NO: 11 and 12) or the signal $EspF_{20}$ (pEspF-bla: SEQ ID NO: 9 and 10) as a positive control.

Figure 12:
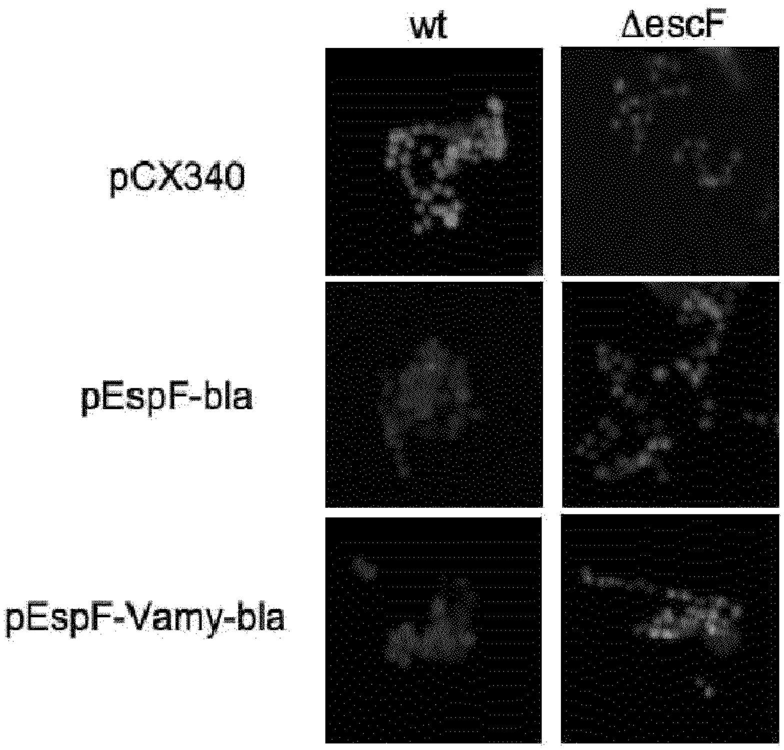
FIG. 12. Translocation test of β-lactamase to HeLa cells. HeLa cells cultivated in vitro were infected with wild EPEC strains (wt) and mutants in T3SS (ΔescF) with the indicated plasmids (pCX340, pEspF-bla and pEspF-Vamy-bla) and incubated with the CCF2/AM substrate. The HeLa cells appear in green when the CCF2/AM substrate has not been hydrolyzed by the β-lactamase and in blue in the opposite case, indicating a positive translocation of the fusion with β-lactamase.

HeLa cells were infected with EPEC bacteria, wild and mutant ΔescF, transformed with each one of these three plasmids. After inducing with IPTG the expression of the fusion antibodies, the substrate CCF2/AM was added to check whether there was β-lactamase activity in the cytoplasm of the HeLa cells. Thus, it was possible to check through fluorescence microscopy (FIG. 12) that the HeLa cells infected with the wild EPEC bacteria and transformed with the plasmids pEspF-Vamy-bla or pEspF-bla emitted in blue (therefore, showed β-lactamase activity) whereas those infected with wild EPEC bacteria with the pCX340 vector, or with any of the plasmids in the case of the mutants ΔescF, emitted in green and therefore, had not translocated the fusion antibody with β-lactamase.

Figure 13:
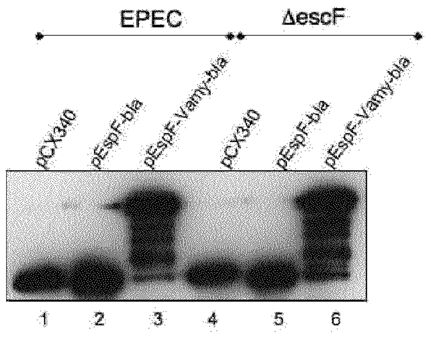
FIG. 13. Expression of the fusions with β-lactamase used in the translocation test (FIG. 12). Western blot of the whole cell lysates using the mAb (monoclonal antibody) anti-β-lactamase as the primary antibody, and an anti-mouse Ig-POD as secondary.

The expression of the fusion antibodies that contained β-lactamase in all the bacteria used was checked by Western blot with anti-β-lactamase antibodies (FIG. 13). Therefore, this experiment proved for the first time that an antibody $V_{HH}$ (e.g. the Vamy clone) could be translocated to the cytoplasm of a eukaryotic cell from wild EPEC strains using the T3SS.

Next, it was decided to investigate whether the fusion antibodies EspF-$V_{HH}$ were capable of recognizing their specific antigen once injected into the cytoplasm of the eukaryotic cell. One way of obtaining evidence of the binding of an intracellular antigen to the fusion antibodies EspF-$V_{HH}$ was to demonstrate the co localization of the antigen and the fusion antibody in the cytoplasm of the eukaryotic cell by means of fluorescence and confocal microscopy. It was possible to use the fusion antibodies EspF-Vgfp in order to check whether they were capable of binding to the protein GFP expressed heterologously in the cytoplasm of HeLa cells. Since the intention was to be able to detect the colocalization of the antigen and antibody, the anchoring of the GFP to a specific point of the cell was first required. To do this fusions of GFP were used to the protein GGA2, a clathrin receptor located on the cytoplasmic face of the membranes of the Golgi apparatus[39]. To detect the fusion antibodies EspF-$V_{HH}$ indirect immunofluorescence was used with the mAb anti-E-tag and a secondary anti-mouse IgG antibody marked with Alexa-594, a fluorophore that emits in red and whose fluorescence is clearly distinguishable from the green emission of the GFP. As a negative control the fusion antibody EspF-Vamy was used, which does not bind to the GFP antigen.

Figure 14:
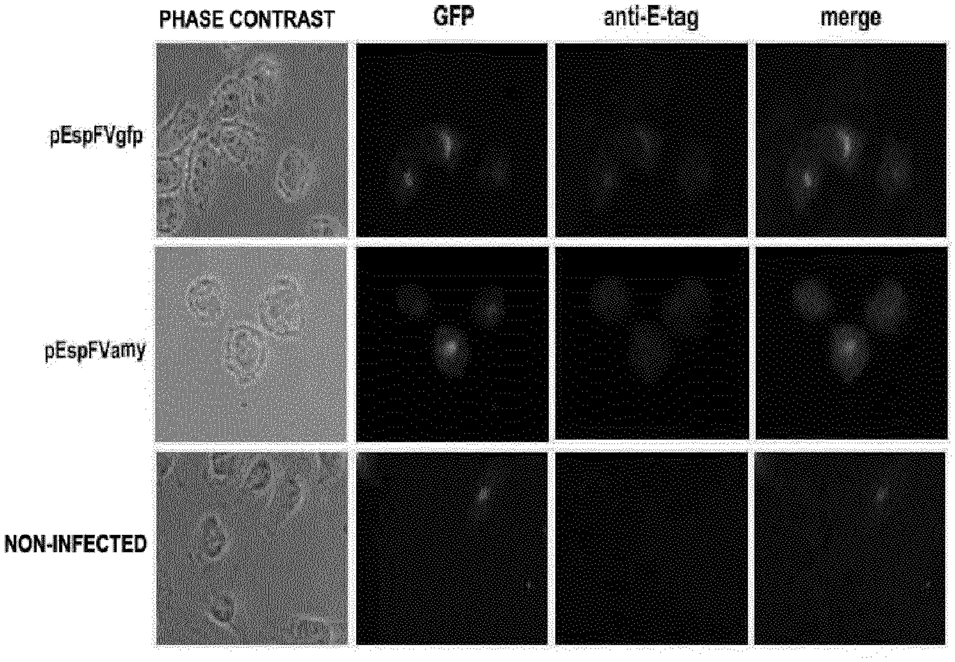
FIG. 14. Intracellular activity of the fusions EspF-$V_{HH}$. Colocalization of GGA2-GFP and the EspF-Vgfp fusion determined by fluorescence microscopy. HeLa cells in culture transfected with the plasmid pGFP-GGA2, were infected (or not) with EPEC with the plasmids pEspF-Vgfp or pEspF-Vamy (as shown). The phase contrast and fluorescence microscopy images appear in green (GFP), marking the GGA2-GFP fusion, and in red (anti-E-tag) marking the EspF-$V_{HH}$ fusions. The mixture of both colors appears in the column on the right.

Therefore, the HeLa cells were transfected in culture with a plasmid that expresses the fusion protein GGA2-GFP and subsequently these cultures were infected with EPEC bacteria that expressed the fusion antibodies EspFVgfp or EspF-Vamy. The HeLa cells were fixed and processed for fluorescence microscopy after staining with the antibodies anti-E-tag and anti-mouse IgG-Alexa-594. As can be observed from FIG. 14, it was possible to verify that only in the case of the cells infected with the EPEC strain expressing the fusion antibody EspF-Vgfp could a clear colocalization of the antibody be observed (red; FIG. 14) with the fusion protein GGA2-GFP (green; FIG. 14) which specifically marked a region of membranes near the nucleus and that corresponded to the Golgi apparatus. Meanwhile, in the HeLa cells infected with the bacteria expressing the fusion antibody EspF-Vamy only a vague fluorescence could be observed with the anti-E-tag antibody (red) and that did not co-localize with the position of the fusion protein GGA2-GFP (green). The vague fluorescence in red detected with anti-E-tag in cells infected with EPEC/pEspFVamy was clearly superior to the signal detected in non-infected cells (FIG. 14). Also, thanks to the presence in the cultures of non-transfected HeLA cells, and which therefore did not express the fusion protein, it was possible to verify that the localization of the fusion antibody EspF-Vgfp in the Golgi only occurred if the cell expressed the fusion protein GGA2-GFP, meaning that there was no binding of the fusion antibody EspF-Vgfp to the Golgi membranes in the absence of GGA2-GFP.

Figure 15:
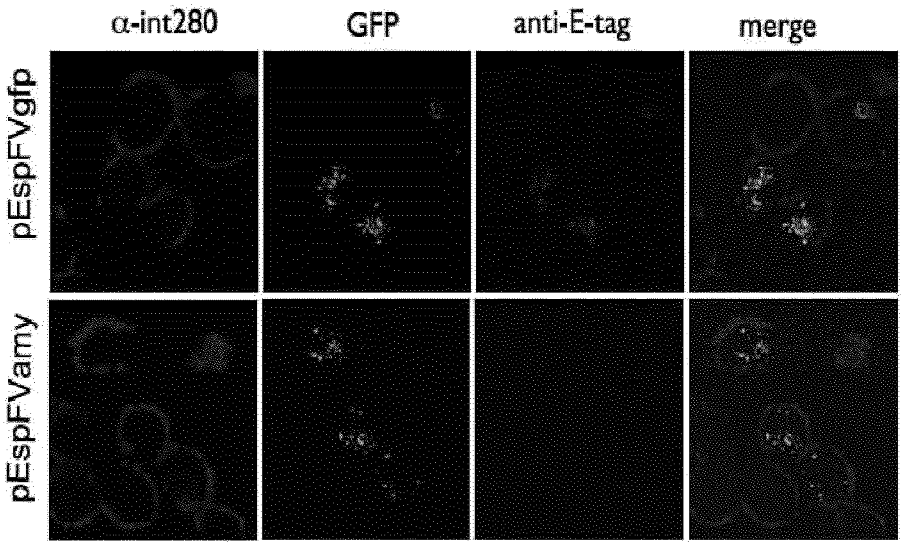
FIG. 15. Intracellular activity of the fusions EspF-$V_{HH}$. Colocalization of GGA2-GFP and the fusion EspF-Vgfp determined by confocal microscopy. HeLa cells in culture transfected with the plasmid pGFP-GGA2, were infected with EPEC with the plasmids pEspF-Vgfp or pEspF-Vamy (as shown). The confocal microscopy images are shown corresponding to green (GFP), marking the GGA2-GFP fusion, red (anti-E-tag) marking the EspF-$V_{HH}$ fusions, and blue (anti-Int280) marking the Intimin present on the surface of EPEC. The mixture of the three colors appears in the column on the right.

It was possible to verify these results through confocal microscopy (FIG. 15) guaranteeing the colocalization of the fluorescence signals of the GFP and EspF-Vgfp. In these images, as well as the signals of the fusions EspF-Vgfp (red) and GGA2-GFP (green), a specific EPEC stain was included, with a polyclonal rabbit antibody anti-$int280_{EPEC}$, which marks the intimin protein present on the surface of bacteria, and as secondary a conjugate anti-IgG rabbit-Alexa 647 (FIG. 15; blue signal).

Finally, in order to obtain unequivocal evidence of the direct interaction between the fusion antibody EspF-Vgfp and the antigen GGA2-GFP experiments of co-immunoprecipitation were carried out with the mAb anti-E-tag. To this effect clarified cell lysates were obtained (without nuclei or bacteria) from HeLa cells expressing the fusion protein GGA2-GFP and infected with EPEC/pEspFVgfp or EPEC/pEspFVamy (as in the previous experiment; see Materials and Methods). As an additional control, a cell lysate was obtained of a HeLa cell culture non-transfected with the fusion protein GGA2-GFP (NT) and infected with EPEC/pEspFVgfp. These protein extracts were incubated with mAb anti-E-tag joined covalently to a Sepharose resin with protein G. The resin was recovered through gentle centrifuging, it was washed to eliminate proteins not bound by the anti-E-tag antibody and the proteins immunoprecipitated (IP) by the mAb anti-E-tag were eluted with an acid pH (0.1 M glycine; pH 2.5). The presence of the fusion antibodies EspF-Vgfp and EspF-Vamy and the fusion protein in the result of the immunoprecipitation was analyzed using Western blots developed with mAb anti-E-tag or anti-GFP (FIG. 16A).

Figure 16:
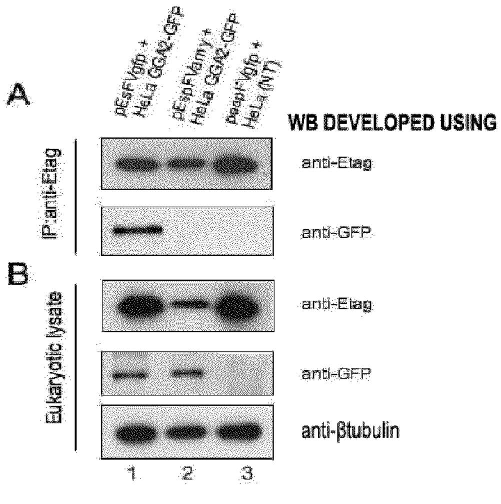
FIG. 16. Immunoprecipitation tests. A) Immunoprecipitation with anti-E-tag mAb bound to protein G-Sepharose of HeLa cell lysates expressing GGA2-GFP, or non-transfected controls (NT), obtained following infection with EPEC transformed with the plasmids pEspF-Vgfp or pEspF-Vamy. The Western blots of the immunoprecipitated proteins are shown developed with anti-E-tag mAb or anti-GFP mAb. (B) Western blots of the eukaryotic lysates used in the immunoprecipitation developed with the mAbs anti-E-tag, anti-GFP and anti-β-tubulin.

As can be seen, the fusion antibodies EspF-Vgfp and EspF-Vamy are found in the protein IP (immunoprecipitation) with anti-E-tag at similar levels (FIG. 16A). However, fusion protein GGA2-GFP only co-immunoprecipitated with the fusion antibody EspF-Vgfp (FIG. 16A, lane 1) and not with the fusion antibody EspF-Vamy (lane 2). The presence of the proteins in the cell lysates that were used was developed using Western blots with anti-E-tag or anti-GFP (FIG. 16B). An anti-β-tubulin antibody was used as internal control of the load in the lysates. Therefore, the experiments of antigen-antibody co-immunoprecipitation, together with those of colocalization in vivo, demonstrate that the fusion antibodies EspF-$V_{HH}$ injected by the EPEC T3SS are functional inside a eukaryotic cell and are capable of recognizing their antigen.

Materials and Methods

Bacterial Strains and Growth Conditions

The bacterial strains used in this study are described in Table 1. The bacteria were grown at 37° C. with aeration in Luria-Bertani (LB) medium or in Dubelcco's modified Eagle's medium (DMEM), supplemented with ampicillin (150 μg $ml^{-1}$) or tetracycline (10 μg $ml^{-1}$), when necessary for the selection of plasmids (see Chaprentier (J Bacteriol 186, 5486-5495 (2004)) and Garmendia (Cell Microbiol 6, 1167-1183 (2004)) which are incorporated by reference herein for their teachings regarding the same). To induce the strains inoculants were placed in LB with the appropriate antibiotic and they were allowed to grow during one night, and the following day 1:50 was diluted in DMEM and they were left growing at 37° C. with agitation up to $DO_{600}$=0.5, at this point a concentration of 0.1 mM of isopropyl β-D-1-thiogalactopyranoside (IPTG) was added and they were left inducing during another 4 hours in the same growth conditions (see Chaprentier (J Bacteriol 186, 5486-5495 (2004)) and Garmendia (Cell Microbiol 6, 1167-1183 (2004)) which are incorporated by reference herein for their teachings regarding the same).

Plasmids

The plasmids used in this work are summarized in Table 1. The construction details of the most relevant plasmids in this work are described below. Standard DNA manipulation and amplification techniques were used. The plasmid pespFVamy (Table 1) is a derivative of pSA10 (see Schlosser-Silverman (J Bacteriol 182, 5225-5230 (2000)) which is incorporated by reference herein for its teachings regarding the same), a vector that contains a multiple cloning site under the control of the promoter Ptac. In this site a fragment of 549 pb was cloned that encoded the $V_{HH}$ anti-amylase (Vamy) fused to the type III secretion signal of 20 amino acids of espF and marked with a sequence of 6 histidines and one E epitope on end 3'. This fragment was amplified by fusion PCR (polymerase chain reaction) of two different fragments. One of them, the EspF secretion signal, was amplified from the genomic DNA of the strain EDL933stx using the primers R1-Xb-SD-EspF and SfiI-espF (Table 2) giving rise to a fragment of 119 pb. The other fragment used in the fusion, of 517 pb (pair bases), is the one corresponding to Vamy with the epitopes 6×his and E on end 3', which was amplified from the plasmid pEHLYA4SD-Vamy (Table 1) using the primers SfiI-Vamy and R1-Stop-E (Table 2). Both fragments were fused by PCR using oligos R1-Xb-SD-EspF and R1-Stop-E (Table 2) for the amplification. The final product of the fusion (of 560 pb) was digested by EcoRI and inserted in the same restriction site of the pSA10 choosing the orientation that situated the gene under the control of the promoter Ptac.

The plasmid pespFVgfp was obtained by replacing through SfiI-NotI digestion, the segment encoding Vamy of the plasmid pespFVamy with the segment encoding Vgfp. The Vgfp segment was obtained from the plasmid pcAbGFP4 (transferred by Dr. Serge Muyldermans, VIB, Brussels) through PCR with the primers Vhh-sfil2 and Vhh-NotI2 (Table 2). The amplified fragment was digested with SfiI and NotI and a digested fragment of 358 pb was linked with T4 ligase to the vector skeleton pespFVamy without the Vamy fragment (~4.3 kb).

The plasmids pEspF-bla and pEspF-Vamy-bla are derivatives of pCX340 (see Charpentier (J Bacteriol 186, 5486-5495 (2004)) incorporated by reference herein for its teachings regarding the same), a vector used for carrying out fusions to β-lactamase TEM (blaM) without signal peptide (Table 1). The first, pEspF-bla, contains the N-terminal signal of EspF (SS) fused to the β-lactamase. The SS of EspF was amplified from the genomic DNA of EDL933stx with the oligonucleotides NdeI-espF and EcoRI-espF (Table 2) giving rise to a fragment of 83 pb. At the same time, the segment encoding the β-lactamase from pCX340 was amplified with the primers EcoRI-TEM and BamHI-Tetra (Table 2), which gave rise to a fragment of 1.2 kb. These fragments were fused by PCR giving rise to a fragment of 1.3 kb which, following digestion with NdeI and BamHI, was linked to the skeleton of the vector pCX340 previously digested with NdeI and BamHI. In the plasmid pCX340 the hybrid $EspF_{20}$-Vamy was inserted, which was amplified by PCR of the plasmid pEspF-Vamy (Table 1) using the primers NdeI-espF and EcoRI-Vamy-espF (Table 2) and subsequently digested with NdeI and EcoRI and linked to the skeleton of the vector pCX340, also digested by these enzymes.

Preparation of Protein Samples, Electrophoresis and Western Blot

The whole cell lysates were prepared from *E. coli* EPEC or EHEC cells gathered through centrifugation (4000 g, 5 min) based on 1 ml of culture induced and resuspended in 100 μl of PBS. Following resuspension the same volume of SDS-PAGE 2× load buffer was added to the mixture (see below). The samples were boiled during 10 minutes, briefly sonicated (5 seconds; Labsonic B Braun) to reduce viscosity and finally centrifuged (14000 g, 5 min) to separate peptidoglican residues before loading into the sample wells of acrylamide-SDS gel (SDS-PAGE). Standard methods were used for the electrophoresis and detection by Western blot.

The supernatants obtained from the induction in strains EPEC and EHEC transformed with the different plasmids were filtered using always PVDF (polyvinylidene fluoride) (Millipore) filters with pores of 0.22 μm, and 1 mM of phenylmethylsulfonyl fluoride (PMSF) were added to them as a serin-protease inhibitor. The samples of the supernatants were prepared for electrophoresis in two ways. In one of them 1 ml of supernatant was precipitated with TCA (trichloroacetic; 10% p/v final) during one hour in ice, the precipitated proteins were recovered through centrifugation (14000 g, 15 min), the pellets obtained were washed in cold acetone (−20° C.) and centrifuged again (14000 g, 15 min) and the resulting pellet was resuspended in 40 μl of TrisHCl 250 mM (pH 7.5), SDS (sodium dodecyl sulfate) 2%, and then 40 μl of SDS-PAGE 2× buffer was added. Alternatively, the filtered supernatants were mixed directly with the SDS-PAGE 2× loading buffer. In both cases, they were boiled during 10 minutes before loading the SDS-PAGE gels.

The SDS-PAGE (sodium dodecyl sulfate polyacrylamide gel electrophoresis) polyacrylamide gels (acrylamide to bisacrylamide 29:1 (w/w); BioRad) were made using 4% in the concentrating gel and 10 or 12% in the separating gel and the electrophoresis system Miniprotean III (BioRad) was used. The SDS-PAGE load buffer was prepared with the following composition (1×): TrisHCl 60 mM (pH 6.8), SDS 1% (p/v), glycerol 5% (v/v), bromophenol blue 0.005% (p/v) and 2-mercaptoethanol 1% (v/v). The proteins present in the acrylamide gels were stained in blue with Coomassie or were used in Western blot for detection with specific antibodies, for which they were transferred to a PVDF membrane (Immobilon-P, Millipore) using semi-dry transfer equipment (Bio-Rad) and the standard protocols. For immunodetection of the proteins with epitope E, the membranes were incubated for 1 hour at room temperature with anti-E-tag mAb-conjugated with peroxidase (POD) (1:5000) (GE Amersham Biosciences). The GroEL protein of *E. coli* was detected with an anti-GroEL-POD conjugated antibody (1:5000) (Sigma). The β-lactamase protein was detected with anti-β-lactamase (1:1000) The β-lactamase protein was detected with anti-β-lactamase (1:1000) (QED Bioscience) mouse monoclonal as primary antibody and anti-mouse IgG-POD (1:5000) (Sigma) as secondary antibody. The GFP protein fused to GGA2 was detected with the antibody anti-GFP (1:1000) (Roche) mouse monoclonal as primary antibody and anti-mouse IgG-POD (1:5000) (Sigma) as secondary antibody. The protein β-tubulin with antibody mAb anti-β-tubulin (transferred by Dr. Francisco García del Portillo, CNB-CSIC)

and anti-mouse IgG-POD (Sigma) as secondary antibody. The membranes were blocked with 3% skimmed milk in PBS, washed in PBS with 0.1% Tween-20, and developed with luminol and hydrogen peroxide ($H_2O_2$) as described in Jurado. (J Mol Biol 320, 1-10. (2002)) which is incorporated by reference herein for its teachings regarding the same.

ELISA Tests

The general conditions of ELISA have been described previously. Immunoadsorption plates of 96 wells (Maxisorp, Nunc) were coated with different antigens at 10 μg/ml in PBS. These antigens were: α-amylase (Sigma), the green fluorescent protein GFP (Upstate) and bovine seroalbumin (BSA, Roche). They were blocked for 2 h with 3% skimmed milk in PBS, then as primary antibody the supernatants with the secreted $V_{HH}$ or the result of their purification was used, and as secondary antibody the anti-E-tag mAb-POD (GE Amersham Bioscience) 1:2000 in milk at 3%. After development with o-phenylenediamine (OPD, Sigma) and $H_2O_2$ (Sigma) the absorbance at 490 nm was determined in a plate reader (Microplate reader, BioRad).

Purification of $V_{HH}$ Antibodies 200 ml of supernatant of the culture medium resulting from the induction of the EPEC strain with the plasmids pespF-Vamy or pespFVgfp was balanced to contain PBS 1× and was incubated overnight at 4° C. with the metal affinity resin (Talon, Clontech), following incubation the resin was washed four times with PBS containing 5 mM of Imidazole (10 ml each time) and eluted in aliquots of 1 ml with PBS containing 100 mM of Imidazole (10 aliquots). The antibodies thus eluted were stored at 4° C. In order to analyze the protein content of the aliquots SDS-PAGE 2× load buffer was added to 10 μl of each aliquot and analyzed by SDS-PAGE and Western blot.

Solubility Test

The supernatant of the induction of the $V_{HH}$ anti-GFP and anti-amylase was centrifuged at high speed (100,000 g) at 4° C. during 1 hour in an ultra-centrifuge (Beckman). The resulting pellets were resuspended for the same final volume as the supernatant, and a sample of each was analyzed by SDS-PAGE and Western blot.

In Vitro Cell Cultures and Transfection and Infection Tests

The HeLa cells were grown in DMEM, supplemented with bovine fetal serum at 10% and 2 mM of glutamine, at 37° C. and with 5% $CO_2$. The cells were planted in round coverslips with a 13 mm diameter placed on slides with a 6 cm diameter (8 coverslips per slide) with a density of $15\times10^6$ cells per slide 20 h before transfection, they were transfected using the calcium phosphate method described in Ausubel F. M. et al. Current Protocols in Molecular Biology. (John Wiley & Sons, New York; 1994 (which is incorporated by reference herein for its teachings regarding the same) using 6 μg of plasmid per slide, 22 hours later the medium with the calcium phosphate crystals was removed and washed 3 times with PBS, then the coverslips were moved to a 24-well plate, where 1 coverslip was placed per well with 1 ml of complete medium in each one, one hour later 20 μl of a bacterial culture were taken with a $DO_{600}\approx2.5$ (grown all night) and was added to each one of the wells, the infection was allowed to start during 1 hour and 15 min to allow time for the bacteria to attach to the surface of the cells, at this point IPTG was added for a final concentration of 0.1 mM and the infection was allowed to continue during another 3.5 hours.

Translocation of Hybrids with β-Lactamase

The methods described in Charpentier (J Bacteriol 186, 5486-5495 (2004)) which is incorporated in by reference for its teachings regarding the same were used. Cultures of EPEC grown overnight were diluted 1:100 in 5 ml of complete DMEM and were incubated at 37° C. in an incubator with an atmosphere of 5% $CO_2$ during 3.5 hours (pre-activation) in a 50 ml Falcon (trademark) tube without agitation. The HeLa cells, grown in slides with sample cells (Falcon) in DMEM complete medium, were infected with 50 μl of a culture of pre-activated bacteria ($D.O._{600\ nm}$~0.5) and at the same time IPTG 1 mM final concentration was added and left incubating for 90 minutes more, then the medium with the bacteria was removed and washed 3 times with Hank's balance salt solution (HBSS), upon finishing the third wash 200 μl of HBSS was added and 40 μl of the substrate for the β-lactamase CCF2/AM (K1024, Invitrogen), the cells were incubated with this mixture during 2.5 hours at room temperature in the dark. Subsequently, the sample cells were removed from the slide, washed 3 times with HBSS and the coverslips were placed for analysis in a fluorescence microscope Nikon Eclipse E600 using the set of filters UV-2ª (330-380 nm excitation). The images were taken using a Nikon Digital DXM1200 camera.

Immunofluorescence Microscopy

The methods described in Garmendia (Cell Microbiol 6, 1167-1183 (2004)) which is incorporated in by reference for its teachings regarding the same were used. Following infection, the monolayers of HeLa cells were washed 3 times with PBS and left fixing with formaldehyde at 3.6% (v/v) for 20 minutes, then they were washed 3 times with PBS. For permeabilization the coverslips were incubated with 0.1% Triton X-100 (Sigma) in PBS during 20 minutes. The antibodies were diluted in 10% goat serum in PBS, the primary antibodies were incubated with the coverslips during 1 hour, following incubation they were washed 3 times with PBS and were incubated for 45 minutes with the secondary antibodies, then they were washed again 3 times and were mounted on the slides using the mounting medium (Vectashield). The antibodies and reagents used were: anti-int280$_{EPEC}$ (rabbit polyclonal) and anti-Etag m-Ab (GE Amersham Bioscience) with dilutions of 1:400 and 1:100 respectively as primary antibodies. As secondary antibodies a goat anti-mouse IgG antibody conjugated with Alexa 594 (Molecular Probes) was used, which emits in red, and a goat anti-rabbit IgG conjugated with Alexa 647, which emits in far red and transforms to blue with the confocal microscopy software. Both were used with a dilution of 1:500. The samples were analyzed using a fluorescence microscope Olympus BX61 and a confocal system (Radiant 2100 System BioRad) complemented with an inverted microscope (Zeiss Axiovert 200).

Immunoprecipitation Tests

The HeLa cells were grown on plates of 150 mm in diameter, the following day with a confluence of 70% they were transfected with 30 μg of DNA (pGFP-GGA2) through the calcium phosphate method, 24 hours later they were infected with EPEC (containing the indicated plasmids) as described above, then the cells were scraped and gathered in a buffer for their mechanical lysis as described in Gauthier (Infect Immun 68, 4344-4348 (2000)) which is incorporated herein by reference for its teachings regarding the same. The result of the lysis was centrifuged at 3000 g×15 min in order to eliminate non-broken cells, nuclei and bacteria. To the supernatant of this centrifugation (considered cell lysate) 40 μl was added of protein G-Sepharose resin (Sigma) which contained the antibody mAb anti-E-tag bound covalently through treatment with the crosslinking agent DMP (Dimethyl Pimelimidate Dihydrochloride, Sigma), following the protocol recommended by (GE Amersham Bioscience). After 16 hours of binding at 4° C. in an orbital agitator, the resin was recovered through centrifugation (2000 g, 1 min) and was washed 3 times with sodium phosphate buffer 200 mM (pH 8.2). Finally, the protein bound to the resin with anti-E-tag was eluted with 60 μl Glycine 0.1 M pH 2.8 (10 min at RT) and after eliminating the resin through centrifugation, the supernatant was balanced with 30 μl of phosphate buffer pH 8.2 and mixed with SDS-PAGE buffer to carry out the Western blot.

Based on the foregoing, exemplary embodiments described herein also include, without limitation, a microorganism comprising a type III protein secretion and injection system (T3SS) and a gene construct wherein said gene construct includes a DNA sequence encoding the secretion signal region (SS)SEQ ID NO: 5 and wherein said sequence encoding said SS is linked to a DNA sequence encoding an antibody.

In another exemplary embodiment the microorganism is a Gram negative bacteria. In another exemplary embodiment the Gram negative bacteria is an enteropathogenic (EPEC) and/or enterohaemorrhagic (EHEC) strain of *Escherichia coli*.

In another exemplary embodiment the secretion signal recognised by said T3SS system is one or more of: SEQ ID NO: 5; a fragment of SEQ ID NO: 5;
a peptide, protein or RNA of a natural effector of T3SS; and
a peptide, protein or RNA of a synthetic effector of T3SS.

In another exemplary embodiment the functionally active antibody is a recombinant antibody or a miniantibody that maintains at least one variable domain including the antigen-binding and wherein said antibody is a Fab antibody, a F(ab')2 antibody, a scFv antibody, or a single-domain recombinant antibody (dAbs).

In another exemplary embodiment the single-domain antibody comprises a heavy-chain variable domain (VH) or a light-chain variable domain (VL), or is a recombinant antibody of camelids (VHH), a recombinant antibody of humanized camelids, a recombinant antibody of other camelised species, or a single-domain IgNAR antibody of a cartilaginous fish.

In another exemplary embodiment the gene construct encodes T3SS (SEQ ID NO: 5) and a single-domain $V_{HH}$ dAb antibody.

Exemplary embodiments disclosed herein also include gene constructs. In one exemplary embodiment, the gene construct comprises (i) SEQ ID NO: 5 or an amino acid sequence with at least 80% homology to SEQ ID NO: 5 and (ii) a DNA sequence encoding a functionally active antibody.

In another exemplary embodiment the sequence encoding the functionally active antibody comprises SEQ ID NO: 1 and/or SEQ ID NO: 3.

In another exemplary embodiment there is a linker sequence between the sequences encoding the SS and the antibody.

In another exemplary embodiment the gene construct is within an expression vector.

In another exemplary embodiment the gene construct comprises SEQ ID NO: 1 and SEQ ID NO: 3, corresponding respectively to pEspFVamy and to pEspFVgfp.

In another exemplary embodiment the gene construct encodes SEQ ID NO: 6.

Exemplary embodiments disclosed herein also include antibodies. In one exemplary embodiment, the antibody is linked to an SS wherein said SS comprises SEQ ID NO: 5 or a fragment of SEQ ID NO: 5.

In another exemplary embodiment the antibody is a Fab antibody, a F(ab')2 antibody, a scFv antibody, or a single-domain recombinant antibody (dAbs).

In another exemplary embodiment the antibody is a $V_{HH}$ camel antibody.

In another exemplary embodiment the antibody is encoded at least in part by SEQ ID NO: 1 or SEQ ID NO: 3. In another exemplary embodiment the antibody is encoded at least in part by SEQ ID NO: 1 and SEQ ID NO: 3.

In another exemplary embodiment the antibody comprises a heavy-chain variable domain (VH) or a light-chain variable domain (VL), or is a recombinant antibody of camelids (VHH), a recombinant antibody of humanized camelids, a recombinant antibody of other camelised species, or a single-domain IgNAR antibody of a cartilaginous fish.

Unless otherwise indicated, all numbers expressing quantities of ingredients, properties such as molecular weight, reaction conditions, and so forth used in the specification and claims are to be understood as being modified in all instances by the term “about.” Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms “a,” “an,” “the” and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., “such as”) provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

TABLE 1

Bacterial strains and plasmids

| Name | Description and main characteristics | References |
|---|---|---|
| **Strains** | | |
| EDL933stx | EHEC O157:H7 stx1 stx2 | ATCC; Gad Frankel laboratory |
| E2348/69 | EPEC O127:H6 | Mc. Daniel et al. (1995) |
| EDL933 ΔescN::Km | Mutant ΔescN; KmR | Garmendia et al. (2004) |
| E2348/69 ΔescF::Km | Mutant ΔescF; KmR | Wilson et al. (2001) |
| **Plasmids** | | |
| pEHLYA4SD-Vamy | Derivative of pUC19 (ApR) that contains a fusion of Vamy to 6xhis E-tag and the C-terminal domain of hlyA | Luis A. Fernández: laboratory collection |
| pcAbGFP 4 | pHEN6c (ApR) encoding $V_{HH}$ anti-GFP | Serge Muyldermans: laboratory collection |
| pSA10 | Derivative of pKK177-3 (ApR) that contains a $lacI^q$ | Schlosser-Silverman et al. (2000) |
| pEspFVamy | A derivative of pSA10 (ApR) encoding 20aa of espF fused to $V_{HH}$ anti-α-amylase with 6xhis and E-tag | This work |
| pEspFVgfp | A derivative of pSA10 (ApR) encoding 20aa of espF fused to a $V_{HH}$ anti-GFP with 6xhis and E-tag | This work |
| pΔsignVgfp | A derivative of pespFVgfp (ApR) with a deletion in the espF signal | This work |
| pCX340 | A derivative of pBR322 TcR used to generate fusions of genes to bla (β-lactamase) | Charpentier & Oswald (2004) |
| pEspF-bla | A derivative of pCX340 (TcR) with the espF signal (20 aa) fused to β-lactamase | This work |
| pEspF-Vamy-bla | A derivative of pCX340 (TcR) with the hybrid espF(20aa)-Vamy fused to β-lactamase | This work |
| pGGA2-GFP | Vector of eukaryotic expression with a Golgi protein, GGA2, fused on the N-terminal end to GFP | R. Mattera et al. (2003) |

TABLE 2

Oligonucleotides

| Name | Nucleotide sequence (5'-3') |
|---|---|
| RI-XB-SD-espF | CCGGAATTCTCTAGAAAGAGGCATAAATTATGCT TAATGGAATTAGTA |
| Sfil-espF | CTGCACCTGAGCCATGGCCGGCTGGGCCGCTGCG ATACCTACAAGCTGCCGCCCTA |
| Sfil-Vamy | CTTGTAGGTATCGCAGCGGCCCAGCCGGCCATGG CTCAGGTGCAGCTG |
| RI-stop-E | CCGGAATTCTCATTAGGCCGGTTCCAGCGGATCC GGATACGGCAC |
| Vhh-Sfil2 | GTCCTCGCAACTGCGGCCCAGCCGGCCATGGCTC AGGTGCAGCTGGTGGA |
| Vhh-NotI2 | GGACTAGTGCGGCCGCTGAGGAGACGGTGACCTG GGT |

TABLE 2-continued

| Oligonucleotides | |
|---|---|
| Name | Nucleotide sequence (5'-3') |
| NdeI-espF | CCGGATCCATATGCTTAATGGAATTAGTAACGCTGCTTCT |
| EcoRI-EspF | GGTGCGAATTCGCTGCGATACCTACAAGCTGCCGCCCTA |
| EcoRI-TEM | GCGGCAGCTTGTAGGTATCGCAGCGAATTCGCACCCAGAAACGCTGGTGA |
| BamHI-tetra | ATGCGTCCGGCGTAGAGGATCCACAGGACGGGT |
| NdeI-espF-Vamy | GGGAATTCCATATGCTTAATGGAATTAGTAACGCTGCT |
| EcoRI-Vamy-espF | CCGGAATTCGCGGCCGGTTCCAGCGGATCCGGATA |
| Δsign-EcoRI | CCGGAATTCTCTAGAAAGAGGCATAAATTATGGCTCAGGTGCAGCTGG |

The invention claimed is:

1. A microorganism comprising a type III protein secretion and injection system (T3SS) and a gene construct wherein said gene construct includes a DNA sequence encoding the secretion signal region (SS) SEQ ID NO: 5 and wherein said sequence encoding said SS is linked to a DNA sequence encoding an antibody.

2. A microorganism according to claim 1, wherein said microorganism is an enteropathogenic (EPEC) and/or enterohaemorrhagic (EHEC) strain of *Escherichia coli.*

3. A microorganism according to claim 1, wherein the secretion signal recognized by said T3SS system is one or more of the following selected from the group consisting of:

SEQ ID NO: 5;

and a peptide, protein or RNA all corresponding to the DNA sequence of SEQ ID NO: 5.

4. A microorganism according to claim 1, wherein the functionally active antibody is a recombinant antibody or a miniantibody that maintains at least one variable domain including the antigen-binding and wherein said antibody is a Fab antibody, a F(ab')2 antibody, a scFv antibody, or a single-domain recombinant antibody (dAbs).

5. A microorganism according to claim 4, wherein the single-domain antibody comprises a heavy-chain variable domain (VH) or a light-chain variable domain (VL), or is a recombinant antibody of camelids (VHH), a recombinant antibody of humanized camelids, a recombinant antibody of other camelised species, or a single-domain IgNAR antibody of a cartilaginous fish.

6. A microorganism according to claim 1, wherein said gene construct encodes T3SS (SEQ ID NO: 5) and a single-domain $V_{HH}$ dAb antibody.

* * * * *